(12) United States Patent
Juan

(10) Patent No.: US 8,071,372 B2
(45) Date of Patent: Dec. 6, 2011

(54) TUMOR ENDOTHELIAL MARKER 5α MOLECULES AND USES THEREOF

(75) Inventor: Todd Juan, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/853,225

(22) Filed: Aug. 9, 2010

(65) Prior Publication Data

US 2011/0033472 A1  Feb. 10, 2011

Related U.S. Application Data

(62) Division of application No. 10/271,697, filed on Oct. 15, 2002, now Pat. No. 7,771,965.

(60) Provisional application No. 60/329,223, filed on Oct. 12, 2001.

(51) Int. Cl.
*C12N 5/24* (2006.01)
*C07K 16/00* (2006.01)

(52) U.S. Cl. ................... 435/331; 530/350; 530/387.3; 530/387.9; 530/388.2

(58) Field of Classification Search ................ 530/350, 530/387.3, 387, 9, 388.2; 435/331
See application file for complete search history.

(56) References Cited

U.S. PATENT DOCUMENTS

| | | | |
|---|---|---|---|
| 5,763,219 | A | 6/1998 | Keyomarsi |
| 2001/0053519 | A1 | 12/2001 | Fodor et al. |
| 2003/0170838 | A1 | 9/2003 | Mishra et al. |

OTHER PUBLICATIONS

Alberts et al., Molecular Biology of the Cell, Garland Publishing, Inc., pp. 5-7, 1994.
Bergers G.G. et al., "Extrinsic regulators of epithelial tumor progression: metalloproteinases." Current Opinion in Genetics and Development, vol. 10 pp. 120-127, 2000.
Boehinger Mannheim Catalog, p. 557, 1991.
Bowie et al., "Deciphering the Message in Protein Sequences: Tolerance to Amino Acid Substitutions," Science 247, pp. 1306-1310 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue," Journal of Cell Biology, vol. 111(5) Part1, pp. 2129-2138, Nov. 1990.
Colman, P.M. et al., "Effects of amino acid sequence changes on antibody-antigen interactions," Research in Immunology, vol. 145, pp. 33-36, 1994.
Database Gene Bank, AN:AL529331, "Homo sapiens cDNA clone CS0DD002YN14," Li, et al., Feb. 2001.
Database Gene Bank, AN:M88565, "Structure and Expression of the Human p58clk-1 Protein Kinase Chromosomal Gene," Eipers et al., Jan. 1995.
Geraci, M.W., et al., "Gene expression patterns in the lungs of patients with primary pulmonary hypertension: a gene microarray analysis," Circ. Res. vol. 88, pp. 555-562, 2001.
Gene, T., "Systems for identifying new drugs are often faulty," Science, vol. 278, pp. 1041-1042, 1997.
Hurwitz, et al., "Bevacizumab plus Irinotecan, Fluorouracil, and Leucovorin for Metastatic Colorectal Cancer," N. Engl. J. Med. vol. 350(23), pp. 2335-2342, 2004.
Ibragimova, G.T. and Eade, R.C., "Stability of the beta-sheet of the WW domain: A molecular dynamics simulation study," Biophysical Journal, vol. 77(4), pp. 2191-2198, Oct. 1999.
Lazar, E. et al., "Transforming growth factor alpha: mutation of aspartic acid 47 and leucine 48 results in different biological activities," Molecular and Cellular Biology, vol. 8, No. 3, pp. 1247-1252, Mar. 1988.
Lin, M.C. et al., "Structure-function relationships in glucagon: properties of highly purified des-His-1-, monoiodo-, and (des-Asn-28, Thr-29)(homoserine lactone-27)-glucagon ," Biochemistry USA, vol. 14(8), pp. 1559-1563, 1975.
Schwatz G.P., et al., "A superactive insulin: [B10-aspartic acid]insulin(human)," Proc. Natl. Acad. Sci. USA, vol. 84 (18), pp. 6408-6411, 1987.
Skolnick et al., "From genes to protein structure and function: novel applications of computational approaches in the genomic era," Trends in Biology, vol. 18, pp. 34-39, 2000.
St. Croix, B. et al., "Genes expressed in human tumor endothelium," Science, vol. 289(5482), pp. 1197-1202, Aug. 18, 2000.
Takamasa, I., et al., "Construction of Preferential cDNA Microarray Specialized for Human Colorectal Carcinoma: Molecular Sketch of Colorectal Cancer," Biochem. Biophys. Res. Commun. vol. 285, pp. 1244-1249, 2001.
Tockman, M.S., et al., "Considerations in bringing a cancer biomarker to clinical application," Cancer Research, vol. 52, pp. 2711s-2718s, 1992.
Vallon, Mario, et al., "Proteolytically Processed Soluble Tumor Endothelial Marker (TEM) 5 Mediates Endothelial Cell Survival during Angiogenesis by Linking Integrin v 3 to Glycosaminoglycans," J. Biol. Chem., vol. 281(4), pp. 34179-34188, Nov. 10, 2006.
Villaret, Douglas B., et al., "Identification of Genes Overexpressed in Head and Neck Squamous Cell Carcinoma Using a Combination of Complementary DNA Subtraction and Microarray Analysis," Laryngoscope, vol. 110, pp. 374-381, Mar. 2000.
Ward, Development Oncology, Nijhoff Publisher, vol. 21, pp. 91-106, 1985.
Wells, James A., "Additivity of Mutational Effects in Proteins," Biochemistry, vol. 29, pp. 8509-8517, 1990.
Yamamoto, et al., "Direct binding of the human homologue of the drosophila disc large tumor suppressor gene to seven-pass thransmembrane proteins, tumor endothelial marker 5 (TEM5), and a novel TEM5-like protein," Oncogene, vol. 23, pp. 3889-3897, 2004.
Zhang, S., et al., "Microarray analysis of nicotine-induced changes in gene expression in endothelial cells Publication: Physiological genomics," Physiol. Genomics, vol. 5, pp. 187-192, 2001.

*Primary Examiner* — Stephen Rawlings

(74) *Attorney, Agent, or Firm* — John A. Lamerdin

(57) ABSTRACT

The present invention provides Tumor Endothelial Marker 5α (TEM5α) polypeptides and nucleic acid molecules encoding the same. The invention also provides selective binding agents, vectors, host cells, and methods for producing TEM5α polypeptides. The invention further provides pharmaceutical compositions and methods for the diagnosis, treatment, amelioration, or prevention of diseases, disorders, and conditions associated with TEM5α polypeptides.

11 Claims, 14 Drawing Sheets

FIG. 1A

```
gtagagcggc tgctgggacc catgcggccg tgacccccgg ctccctagag gcccagcgca   60
gccgcagcgg acaaaggagc atgtccgcgc cggggaaggc ccgtcctccg gccgccataa  120
ggctccggtc gccgctgggc ccgcgccgcg ctcctgcccg ccgggctccg gggcggcccg  180
ctaggccagt gcgccgccgc tcgccccgca ggccccggcc cgcagc atg gag cca    235
                                                  Met Glu Pro
                                                   1
```

```
ccc gga cgc cgg cgg ggc cgc gcg cag ccg ccg ctg ttg ctg ccg ctc   283
Pro Gly Arg Arg Arg Gly Arg Ala Gln Pro Pro Leu Leu Leu Pro Leu
     5               10                  15 tcg ctg tta gcg ctg ctc gcg ctg ctg gga ggc ggc ggc ggc ggc ggc   331
Ser Leu Leu Ala Leu Leu Ala Leu Leu Gly Gly Gly Gly Gly Gly Gly
 20              25                  30                      35 gcc gcg gcg ctg ccc gcc ggc tgc aag cac gat ggg cgg ccc cga ggg   379
Ala Ala Ala Leu Pro Ala Gly Cys Lys His Asp Gly Arg Pro Arg Gly
             40                  45                  50 gct ggc agg gcg gcg ggc gcc gcc gag ggc aag gtg gtg tgc agc agc   427
Ala Gly Arg Ala Ala Gly Ala Ala Glu Gly Lys Val Val Cys Ser Ser
         55                  60                  65 ctg gaa ctc gcg cag gtc ctg ccc cca gat act ctg ccc aac cgc acg   475
Leu Glu Leu Ala Gln Val Leu Pro Pro Asp Thr Leu Pro Asn Arg Thr
     70                  75                  80 gtc acc ctg att ctg agt aac aat aag ata tcc gag ctg aag aat ggc   523
Val Thr Leu Ile Leu Ser Asn Asn Lys Ile Ser Glu Leu Lys Asn Gly
 85                  90                  95 tca ttt tct ggg tta agt ctc ctt gaa aga ttg gac ctc cga aac aat   571
Ser Phe Ser Gly Leu Ser Leu Leu Glu Arg Leu Asp Leu Arg Asn Asn
100                 105                 110                 115 ctt att agt agt ata gat cca ggt gcc ttc tgg gga ctg tca tct cta   619
Leu Ile Ser Ser Ile Asp Pro Gly Ala Phe Trp Gly Leu Ser Ser Leu
             120                 125                 130 aaa aga ttg gat ctg aca aac aat cga ata gga tgt ctg aat gca gac   667
Lys Arg Leu Asp Leu Thr Asn Asn Arg Ile Gly Cys Leu Asn Ala Asp
         135                 140                 145 ata ttt cga gga ctc acc aat ctg gtt cgg cta aac ctt tcg ggg aat   715
Ile Phe Arg Gly Leu Thr Asn Leu Val Arg Leu Asn Leu Ser Gly Asn
     150                 155                 160 ttg ttt tct tca tta tct caa gga act ttt gat tat ctt gcg tca tta   763
Leu Phe Ser Ser Leu Ser Gln Gly Thr Phe Asp Tyr Leu Ala Ser Leu
 165                 170                 175 cgg tct ttg gaa ttc cag act gag tat ctt ttg tgt gac tgt aac ata   811
Arg Ser Leu Glu Phe Gln Thr Glu Tyr Leu Leu Cys Asp Cys Asn Ile
180                 185                 190                 195
```

FIG. 1B

```
ctg tgg atg cat cgc tgg gta aag gag aag aac atc acg gta cgg gat    859
Leu Trp Met His Arg Trp Val Lys Glu Lys Asn Ile Thr Val Arg Asp
            200                 205                 210 acc agg tgt gtt tat cct aag tca ctg cag gcc caa cca gtc aca ggc    907
Thr Arg Cys Val Tyr Pro Lys Ser Leu Gln Ala Gln Pro Val Thr Gly
            215                 220                 225 gtg aag cag gag ctg ttg aca tgc gac cct ccg ctt gaa ttg ccg tct    955
Val Lys Gln Glu Leu Leu Thr Cys Asp Pro Pro Leu Glu Leu Pro Ser
            230                 235                 240 ttc tac atg act cca tct cat cgc caa gtt gtg ttt gaa gga gac agc   1003
Phe Tyr Met Thr Pro Ser His Arg Gln Val Val Phe Glu Gly Asp Ser
            245                 250                 255 ctt cct ttc cag tgc atg gct tca tat att gat cag gac atg caa gtg   1051
Leu Pro Phe Gln Cys Met Ala Ser Tyr Ile Asp Gln Asp Met Gln Val
260                 265                 270                 275 ttg tgg tat cag gat ggg aga ata gtt gaa acc gat gaa tcg caa ggt   1099
Leu Trp Tyr Gln Asp Gly Arg Ile Val Glu Thr Asp Glu Ser Gln Gly
            280                 285                 290 att ttt gtt gaa aag aac atg att cac aac tgc tcc ttg att gca agt   1147
Ile Phe Val Glu Lys Asn Met Ile His Asn Cys Ser Leu Ile Ala Ser
            295                 300                 305 gcc cta acc att tct aat att cag gct gga tct act gga aat tgg ggc   1195
Ala Leu Thr Ile Ser Asn Ile Gln Ala Gly Ser Thr Gly Asn Trp Gly
            310                 315                 320 tgt cat gtc cag acc aaa cgt ggg aat aat acg agg act gtg gat att   1243
Cys His Val Gln Thr Lys Arg Gly Asn Asn Thr Arg Thr Val Asp Ile
            325                 330                 335 gtg gta tta gag agt tct gca cag tac tgt ccg cca gag agg gtg gta   1291
Val Val Leu Glu Ser Ser Ala Gln Tyr Cys Pro Pro Glu Arg Val Val
340                 345                 350                 355 aac aac aaa ggt gac ttc aga tgg ccc aga aca ttg gca ggc att act   1339
Asn Asn Lys Gly Asp Phe Arg Trp Pro Arg Thr Leu Ala Gly Ile Thr
            360                 365                 370 gca tat ctg cag tgt acg cgg aac acc cat ggc agt ggg ata tat ccc   1387
Ala Tyr Leu Gln Cys Thr Arg Asn Thr His Gly Ser Gly Ile Tyr Pro
            375                 380                 385 gga aac cca cag gat gag aga aaa gct tgg cgc aga tgt gat aga ggt   1435
Gly Asn Pro Gln Asp Glu Arg Lys Ala Trp Arg Arg Cys Asp Arg Gly
            390                 395                 400 ggc ttt tgg gca gat gat gat tat tct cgc tgt cag tat gca aat gat   1483
Gly Phe Trp Ala Asp Asp Asp Tyr Ser Arg Cys Gln Tyr Ala Asn Asp
            405                 410                 415
```

FIG. 1C

```
gtc act aga gtt ctt tat atg ttt aat cag atg ccc ctc aat ctt acc   1531
Val Thr Arg Val Leu Tyr Met Phe Asn Gln Met Pro Leu Asn Leu Thr
420                 425                 430                 435 aat gcc gtg gca aca gct cga cag tta ctg gct tac act gtg gaa gca   1579
Asn Ala Val Ala Thr Ala Arg Gln Leu Leu Ala Tyr Thr Val Glu Ala
                    440                 445                 450 gcc aac ttt tct gac aaa atg gat gtt ata ttt gtg gca gaa atg att   1627
Ala Asn Phe Ser Asp Lys Met Asp Val Ile Phe Val Ala Glu Met Ile
                455                 460                 465 gaa aaa ttt gga aga ttt acc aag gag gaa aaa tca aaa gag cta ggt   1675
Glu Lys Phe Gly Arg Phe Thr Lys Glu Glu Lys Ser Lys Glu Leu Gly
            470                 475                 480 gac gtg atg gtt gac att gca agt aac atc atg ttg gct gat gaa cgt   1723
Asp Val Met Val Asp Ile Ala Ser Asn Ile Met Leu Ala Asp Glu Arg
        485                 490                 495 gtc ctg tgg ctg gcg cag agg gaa gct aaa gcc tgc agt agg att gtg   1771
Val Leu Trp Leu Ala Gln Arg Glu Ala Lys Ala Cys Ser Arg Ile Val
500                 505                 510                 515 cag tgt ctt cag cgc att gct acc tac cgg cta gcc ggt gga gct cac   1819
Gln Cys Leu Gln Arg Ile Ala Thr Tyr Arg Leu Ala Gly Gly Ala His
                    520                 525                 530 gtt tat tca aca tat tca ccc aat att gct ctg gaa gct tat gtc atc   1867
Val Tyr Ser Thr Tyr Ser Pro Asn Ile Ala Leu Glu Ala Tyr Val Ile
                535                 540                 545 aag tct act ggc ttc acg ggg atg acc tgt acc gtg ttc cag aaa gtg   1915
Lys Ser Thr Gly Phe Thr Gly Met Thr Cys Thr Val Phe Gln Lys Val
            550                 555                 560 gca gcc tct gat cgt aca gga ctt tcg gat tat ggg agg cgg gat cca   1963
Ala Ala Ser Asp Arg Thr Gly Leu Ser Asp Tyr Gly Arg Arg Asp Pro
        565                 570                 575 gag gga aac ctg gat aag cag ctg agc ttt aag tgc aat gtt tca aat   2011
Glu Gly Asn Leu Asp Lys Gln Leu Ser Phe Lys Cys Asn Val Ser Asn
580                 585                 590                 595 aca ttt tcg agt ctg gca cta aag aat act att gtg gag gct tct att   2059
Thr Phe Ser Ser Leu Ala Leu Lys Asn Thr Ile Val Glu Ala Ser Ile
                    600                 605                 610 cag ctt cct cct tcc ctt ttc tca cca aag caa aaa aga gaa ctc aga   2107
Gln Leu Pro Pro Ser Leu Phe Ser Pro Lys Gln Lys Arg Glu Leu Arg
                615                 620                 625 cca act gat gac tct ctt tac aag ctt caa ctc att gca ttc cgc aat   2155
Pro Thr Asp Asp Ser Leu Tyr Lys Leu Gln Leu Ile Ala Phe Arg Asn
            630                 635                 640
```

FIG. 1D

```
gga aag ctt ttt cca gcc act gga aat tca aca aat ttg gct gat gat    2203
Gly Lys Leu Phe Pro Ala Thr Gly Asn Ser Thr Asn Leu Ala Asp Asp
    645                 650                 655 gga aaa cga cgt act gtg gtt acc cct gtg att ctc acc aaa ata gat    2251
Gly Lys Arg Arg Thr Val Val Thr Pro Val Ile Leu Thr Lys Ile Asp
660                 665                 670                 675 ggt gtg aat gta gat acc cac cac atc cct gtt aat gtg aca ctg cgt    2299
Gly Val Asn Val Asp Thr His His Ile Pro Val Asn Val Thr Leu Arg
                    680                 685                 690 cga att gca cat gga gca gat gct gtt gca gcc cgg tgg gat ttc gat    2347
Arg Ile Ala His Gly Ala Asp Ala Val Ala Ala Arg Trp Asp Phe Asp
                695                 700                 705 ttg ctg aac gga caa gga ggc tgg aag tca gat ggg tgc cat ata ctc    2395
Leu Leu Asn Gly Gln Gly Gly Trp Lys Ser Asp Gly Cys His Ile Leu
            710                 715                 720 tat tca gat gaa aat atc act acg att cag tgc tac tcc ctt agt aac    2443
Tyr Ser Asp Glu Asn Ile Thr Thr Ile Gln Cys Tyr Ser Leu Ser Asn
    725                 730                 735 tat gca gtt tta atg gat ttg acg gga tct gaa cta tac acc cag gcg    2491
Tyr Ala Val Leu Met Asp Leu Thr Gly Ser Glu Leu Tyr Thr Gln Ala
740                 745                 750                 755 gcc agc ctc ctg cat cct gtg gtt tat act acc gct atc att ctc ctc    2539
Ala Ser Leu Leu His Pro Val Val Tyr Thr Thr Ala Ile Ile Leu Leu
                    760                 765                 770 tta tgt ctc tta gcc gtc att gtc agt tac ata tac cat cac agt ttg    2587
Leu Cys Leu Leu Ala Val Ile Val Ser Tyr Ile Tyr His His Ser Leu
                775                 780                 785 att aga atc agc ctc aag agc tgg cac atg ctt gtg aac ttg tgc ttt    2635
Ile Arg Ile Ser Leu Lys Ser Trp His Met Leu Val Asn Leu Cys Phe
            790                 795                 800 cat att ttc cta acc tgt gtg gtc ttt gtg gga gga ata acc cag act    2683
His Ile Phe Leu Thr Cys Val Val Phe Val Gly Gly Ile Thr Gln Thr
    805                 810                 815 agg aat gcc agc atc tgc caa gca gtt ggg ata att ctt cac tat tcc    2731
Arg Asn Ala Ser Ile Cys Gln Ala Val Gly Ile Ile Leu His Tyr Ser
820                 825                 830                 835 acc ctt gcc aca gta cta tgg gta gga gtg aca gct cga aat atc tac    2779
Thr Leu Ala Thr Val Leu Trp Val Gly Val Thr Ala Arg Asn Ile Tyr
                    840                 845                 850 aaa caa gtc act aaa aaa gct aaa aga tgc cag gat cct gat gaa cca    2827
Lys Gln Val Thr Lys Lys Ala Lys Arg Cys Gln Asp Pro Asp Glu Pro
                855                 860                 865
```

FIG. 1E

```
cca cct cca cca aga cca atg ctc aga ttt tac ctg att ggt ggt ggt    2875
Pro Pro Pro Pro Arg Pro Met Leu Arg Phe Tyr Leu Ile Gly Gly Gly
        870             875             880 atc ccc atc att gtt tgc ggc ata act gca gca gcg aac att aag aat    2923
Ile Pro Ile Ile Val Cys Gly Ile Thr Ala Ala Ala Asn Ile Lys Asn
        885             890             895 tac ggc agt cgg cca aac gca ccc tat tgc tgg atg gca tgg gaa ccc    2971
Tyr Gly Ser Arg Pro Asn Ala Pro Tyr Cys Trp Met Ala Trp Glu Pro
900             905             910             915 tcc ttg gga gcc ttc tat ggg cca gcc agc ttc atc act ttt gta aac    3019
Ser Leu Gly Ala Phe Tyr Gly Pro Ala Ser Phe Ile Thr Phe Val Asn
            920             925             930 tgc atg tac ttt ctg agc ata ttt att cag ttg aaa aga cac cct gag    3067
Cys Met Tyr Phe Leu Ser Ile Phe Ile Gln Leu Lys Arg His Pro Glu
            935             940             945 cgc aaa tat gag ctt aag gag ccc acg gag gag caa cag aga ttg gca    3115
Arg Lys Tyr Glu Leu Lys Glu Pro Thr Glu Glu Gln Gln Arg Leu Ala
        950             955             960 gcc aat gaa aat ggc gaa ata aat cat cag gat tca atg tct ttg tct    3163
Ala Asn Glu Asn Gly Glu Ile Asn His Gln Asp Ser Met Ser Leu Ser
        965             970             975 ctg att tct aca tca gcc ttg gaa aat gag cac act ttt cat tct cag    3211
Leu Ile Ser Thr Ser Ala Leu Glu Asn Glu His Thr Phe His Ser Gln
980             985             990             995 ctc ttg ggg gcc agc ctt act ttg ctc tta tat gtt gca ctg tgg atg    3259
Leu Leu Gly Ala Ser Leu Thr Leu Leu Leu Tyr Val Ala Leu Trp Met
            1000            1005            1010 ttt ggg gct ttg gct gtt tct ttg tat tac cct ttg gac ttg gtt ttt    3307
Phe Gly Ala Leu Ala Val Ser Leu Tyr Tyr Pro Leu Asp Leu Val Phe
            1015            1020            1025 agc ttc gtt ttt gga gcc aca agt tta agc ttc agt gcg ttc ttc gtg    3355
Ser Phe Val Phe Gly Ala Thr Ser Leu Ser Phe Ser Ala Phe Phe Val
            1030            1035            1040 gtc cac cat tgt gtt aat agg gag gat gtt aga ctt gcg tgg atc atg    3403
Val His His Cys Val Asn Arg Glu Asp Val Arg Leu Ala Trp Ile Met
        1045            1050            1055 act tgc tgc cca gga cgg agc tcg tat tca gtg caa gtc aac gtc cag    3451
Thr Cys Cys Pro Gly Arg Ser Ser Tyr Ser Val Gln Val Asn Val Gln
1060            1065            1070            1075 ccc ccc aac tct aat ggg acg aat gga gag gca ccc aaa tgc ccc aat    3499
Pro Pro Asn Ser Asn Gly Thr Asn Gly Glu Ala Pro Lys Cys Pro Asn
        1080            1085            1090
```

FIG. 1F

```
agc agt gcg gag tct tca tgc aca aac aaa agt gct tca agc ttc aaa    3547
Ser Ser Ala Glu Ser Ser Cys Thr Asn Lys Ser Ala Ser Ser Phe Lys
            1095                1100                1105 aat tcc tcc cag ggc tgc aaa tta aca aac ttg cag gcg gct gca gct    3595
Asn Ser Ser Gln Gly Cys Lys Leu Thr Asn Leu Gln Ala Ala Ala Ala
        1110                1115                1120 cag tgc cat gcc aat tct tta cct ttg aac tcc acc cct cag ctt gat    3643
Gln Cys His Ala Asn Ser Leu Pro Leu Asn Ser Thr Pro Gln Leu Asp
    1125                1130                1135 aat agt ctg aca gaa cat tca atg gac aat gat att aaa atg cac gtg    3691
Asn Ser Leu Thr Glu His Ser Met Asp Asn Asp Ile Lys Met His Val
1140                1145                1150                1155 gcg cct tta gaa gtt cag ttt cga aca aat gtg cac tca agc cgc cac    3739
Ala Pro Leu Glu Val Gln Phe Arg Thr Asn Val His Ser Ser Arg His
            1160                1165                1170 cat aaa aac aga agt aaa gga cac cgg gca agc cga ctc aca gtc ctg    3787
His Lys Asn Arg Ser Lys Gly His Arg Ala Ser Arg Leu Thr Val Leu
        1175                1180                1185 aga gaa tat gcc tac gat gtc cca acg agc gtg gaa gga agc gtg cag    3835
Arg Glu Tyr Ala Tyr Asp Val Pro Thr Ser Val Glu Gly Ser Val Gln
    1190                1195                1200 aac ggc tta cct aaa agc cgg ctg ggc aat aac gaa gga cac tcg agg    3883
Asn Gly Leu Pro Lys Ser Arg Leu Gly Asn Asn Glu Gly His Ser Arg
1205                1210                1215 agc cga aga gct tat tta gcc tac aga gag aga cag tac aac cca ccc    3931
Ser Arg Arg Ala Tyr Leu Ala Tyr Arg Glu Arg Gln Tyr Asn Pro Pro
1220                1225                1230                1235 cag caa gac agc agc gat gct tgt agc aca ctt ccc aaa agt agc aga    3979
Gln Gln Asp Ser Ser Asp Ala Cys Ser Thr Leu Pro Lys Ser Ser Arg
            1240                1245                1250 aat ttt gaa aag cca gtt tca acc act agt aaa aaa gat gcg tta agg    4027
Asn Phe Glu Lys Pro Val Ser Thr Thr Ser Lys Lys Asp Ala Leu Arg
        1255                1260                1265 aag cca gct gtg gtt gaa ctt gaa aat cag caa aaa tct tat ggc ctc    4075
Lys Pro Ala Val Val Glu Leu Glu Asn Gln Gln Lys Ser Tyr Gly Leu
    1270                1275                1280 aac ttg gcc att cag aat gga cca att aaa agc aat ggg cag gag gga    4123
Asn Leu Ala Ile Gln Asn Gly Pro Ile Lys Ser Asn Gly Gln Glu Gly
    1285                1290                1295 ccc ttg ctc ggt acc gat agc act ggc aat gtt agg act gga tta tgg    4171
Pro Leu Leu Gly Thr Asp Ser Thr Gly Asn Val Arg Thr Gly Leu Trp
1300                1305                1310                1315
```

FIG. 1G

```
aaa cac gaa act act gtg taacattgct gggcttccta ggcagaaatt         4219
Lys His Glu Thr Thr Val
              1320 catataaact gtgatactca cattccttga agctatgagc atttaaaaac tgtttacagc 4279 caccataggg attcaaaaga atttggaata aactttgaag ttttggattt tacttatttt 4339 tatccccaaa ttgttgctat tttttaggat ctgaaacaaa atctttctaa aacattgttt 4399 tagttgtcaa agcaccaaca ggacattttg ggatgtgaaa tgtaatttct tggaatctgt 4459 aatttgtact tagtatttca ggcttgtatt taatataata aataggtgtt tgttattgtg 4519 tcaaaaaaaa aaaaaaa                                               4536
```

FIG. 2A

```
cgcgctcct gcccgcccgg gctccggggc ggcccgctag gccagtgcgc cgccgctcgc    60
cccgcaggcc ccggcccgca gc atg gag cca ccc gga cgc cgg cgg ggc cgc   112
                          Met Glu Pro Pro Gly Arg Arg Arg Gly Arg
                           1               5                  10 gcg cag ccg ccg ctg ttg ctg ccg ctc tcg ctg tta gcg ctg ctc gcg   160
Ala Gln Pro Pro Leu Leu Leu Pro Leu Ser Leu Leu Ala Leu Leu Ala
                15                  20                  25 ctg ctg gga ggc ggc ggc ggc ggc ggc gcc gcg gcg ctg ccc gcc ggc   208
Leu Leu Gly Gly Gly Gly Gly Gly Gly Ala Ala Ala Leu Pro Ala Gly
            30                  35                  40 tgc aag cac gat ggg cgg ccc cga ggg gct ggc agg gcg gcg ggc gcc   256
Cys Lys His Asp Gly Arg Pro Arg Gly Ala Gly Arg Ala Ala Gly Ala
        45                  50                  55 gcc gag ggc aag gtg gtg tgc agc agc ctg gaa ctc gcg cag gtc ctg   304
Ala Glu Gly Lys Val Val Cys Ser Ser Leu Glu Leu Ala Gln Val Leu
    60                  65                  70 ccc cca gat act ctg ccc aac cgc acg gtc acc ctg att ctg agt aac   352
Pro Pro Asp Thr Leu Pro Asn Arg Thr Val Thr Leu Ile Leu Ser Asn
 75                  80                  85                  90 aat aag ata tcc gag ctg aag aat ggc tca ttt tct ggg tta agt ctc   400
Asn Lys Ile Ser Glu Leu Lys Asn Gly Ser Phe Ser Gly Leu Ser Leu
                95                 100                 105 ctt gaa aga ttg gac ctc cga aac aat ctt att agt agt ata gat cca   448
Leu Glu Arg Leu Asp Leu Arg Asn Asn Leu Ile Ser Ser Ile Asp Pro
            110                 115                 120 ggt gcc ttc tgg gga ctg tca tct cta aaa aga ttg gat ctg aca aac   496
Gly Ala Phe Trp Gly Leu Ser Ser Leu Lys Arg Leu Asp Leu Thr Asn
        125                 130                 135 aat cga ata gga tgt ctg aat gca gac ata ttt cga gga ctc acc aat   544
Asn Arg Ile Gly Cys Leu Asn Ala Asp Ile Phe Arg Gly Leu Thr Asn
    140                 145                 150 ctg gtt cgg cta aac ctt tcg ggg aat ttg ttt tct tca tta tct caa   592
Leu Val Arg Leu Asn Leu Ser Gly Asn Leu Phe Ser Ser Leu Ser Gln
155                 160                 165                 170 gga act ttt gat tat ctt gcg tca tta cgg tct ttg gaa ttc cag act   640
Gly Thr Phe Asp Tyr Leu Ala Ser Leu Arg Ser Leu Glu Phe Gln Thr
                175                 180                 185 gag tat ctt ttg tgt gac tgt aac ata ctg tgg atg cat cgc tgg gta   688
Glu Tyr Leu Leu Cys Asp Cys Asn Ile Leu Trp Met His Arg Trp Val
            190                 195                 200 aag gag aag aac atc acg gta cgg gat acc agg tgt gtt tat cct aag   736
Lys Glu Lys Asn Ile Thr Val Arg Asp Thr Arg Cys Val Tyr Pro Lys
        205                 210                 215
```

FIG. 2B

```
tca ctg cag gcc caa cca gtc aca ggc gtg aag cag gag ctg ttg aca    784
Ser Leu Gln Ala Gln Pro Val Thr Gly Val Lys Gln Glu Leu Leu Thr
    220             225                 230 tgc gac cct ccg ctt gaa ttg ccg tct ttc tac atg act cca tct cat    832
Cys Asp Pro Pro Leu Glu Leu Pro Ser Phe Tyr Met Thr Pro Ser His
235             240                 245                 250 cgc caa gtt gtg ttt gaa gga gac agc ctt cct ttc cag tgc atg gct    880
Arg Gln Val Val Phe Glu Gly Asp Ser Leu Pro Phe Gln Cys Met Ala
                255                 260                 265 tca tat att gat cag gac atg caa gtg ttg tgg tat cag gat ggg aga    928
Ser Tyr Ile Asp Gln Asp Met Gln Val Leu Trp Tyr Gln Asp Gly Arg
            270                 275                 280 ata gtt gaa acc gat gaa tcg caa ggt att ttt gtt gaa aag aac atg    976
Ile Val Glu Thr Asp Glu Ser Gln Gly Ile Phe Val Glu Lys Asn Met
        285                 290                 295 att cac aac tgc tcc ttg att gca agt gcc cta acc att tct aat att    1024
Ile His Asn Cys Ser Leu Ile Ala Ser Ala Leu Thr Ile Ser Asn Ile
    300                 305                 310 cag gct gga tct act gga aat tgg ggc tgt cat gtc cag acc aaa cgt    1072
Gln Ala Gly Ser Thr Gly Asn Trp Gly Cys His Val Gln Thr Lys Arg
315                 320                 325                 330 ggg aat aat acg agg act gtg gat att gtg gta tta gag agt tct gca    1120
Gly Asn Asn Thr Arg Thr Val Asp Ile Val Val Leu Glu Ser Ser Ala
            335                 340                 345 cag tac tgt ccg cca gag agg gtg gta aac aac aaa ggt gac ttc aga    1168
Gln Tyr Cys Pro Pro Glu Arg Val Val Asn Asn Lys Gly Asp Phe Arg
        350                 355                 360 tgg ccc aga aca ttg gca ggc att act gca tat ctg cag tgt acg cgg    1216
Trp Pro Arg Thr Leu Ala Gly Ile Thr Ala Tyr Leu Gln Cys Thr Arg
    365                 370                 375 aac acc cat ggc agt ggg ata tat ccc gga aac cca cag gat gag aga    1264
Asn Thr His Gly Ser Gly Ile Tyr Pro Gly Asn Pro Gln Asp Glu Arg
380                 385                 390 aaa gct tgg cgc aga tgt gat aga ggt ggc ttt tgg gca gat gat gat    1312
Lys Ala Trp Arg Arg Cys Asp Arg Gly Gly Phe Trp Ala Asp Asp Asp
395                 400                 405                 410 tat tct cgc tgt cag tat gca aat gat gtc act aga gtt ctt tat atg    1360
Tyr Ser Arg Cys Gln Tyr Ala Asn Asp Val Thr Arg Val Leu Tyr Met
            415                 420                 425 ttt aat cag atg ccc ctc aat ctt acc aat gcc gtg gca aca gct cga    1408
Phe Asn Gln Met Pro Leu Asn Leu Thr Asn Ala Val Ala Thr Ala Arg
        430                 435                 440
```

FIG. 2C

```
cag tta ctg gct tac act gtg gaa gca gcc aac ttt tct gac aaa atg    1456
Gln Leu Leu Ala Tyr Thr Val Glu Ala Ala Asn Phe Ser Asp Lys Met
        445                 450                 455 gat gtt ata ttt gtg gca gaa atg att gaa aaa ttt gga aga ttt acc    1504
Asp Val Ile Phe Val Ala Glu Met Ile Glu Lys Phe Gly Arg Phe Thr
    460                 465                 470 aag gag gaa aaa tca aaa gag cta ggt gac gtg atg gtt gac att gca    1552
Lys Glu Glu Lys Ser Lys Glu Leu Gly Asp Val Met Val Asp Ile Ala
475                 480                 485                 490 agt aac atc atg ttg gct gat gaa cgt gtc ctg tgg ctg gcg cag agg    1600
Ser Asn Ile Met Leu Ala Asp Glu Arg Val Leu Trp Leu Ala Gln Arg
                495                 500                 505 gaa gct aaa gcc tgc agt agg atc gtg cag tgt ctt cag cgc att gct    1648
Glu Ala Lys Ala Cys Ser Arg Ile Val Gln Cys Leu Gln Arg Ile Ala
            510                 515                 520 acc tac cgg cta gcc ggt gga gct cac gtt tat tca aca att gac ttt    1696
Thr Tyr Arg Leu Ala Gly Gly Ala His Val Tyr Ser Thr Ile Asp Phe
        525                 530                 535 tca agt att cac cca ata ttg ctc tgg aag ctt atg tca tca agt cta    1744
Ser Ser Ile His Pro Ile Leu Leu Trp Lys Leu Met Ser Ser Ser Leu
    540                 545                 550 ctg gct tca cgg gga tgacctgtac cgtgttccag aaagtggcag cctctgatcg    1799
Leu Ala Ser Arg Gly
555 tacaggactt tcggattatg ggaggcggga tccagaggga aacctggata agcagctgag  1859 ctttaagtgc aatgtttcaa atacattttc gagtctggca ctaaagaata ctattgtgga  1919 ggcttctatt cagcttcctc cttcccttt ctcaccaaag caaaaaagag aactcagacc   1979 aactgatgac tctctttaca agcttcaact cattgcattc cgcaatggaa agcttttcc   2039 agccactgga aattcaacaa atttggctga tgatggaaaa cgacgtactg tggttacccc   2099 tgtgattctc accaaaatag atggtgtgaa tgtagatacc caccacatcc ctgttaatgt   2159 gacactgcgt cgaattgcac atggagcaga tgctgttgca gcccggtggg atttcgattt   2219 gctgaacgga caaggaggct ggaagtcaga tgggtgccat atactctatt cagatgaaaa   2279 tatcactacg attcagtgct actcccttag taactatgca gttttaatgg atttgacggg   2339 atctgaacta tacacccagg cggccagcct cctgcatcct gtggtttata ctaccgctat   2399 cattctcctc ttatgtctct tagccgtcat tgtcagttac atataccatc acagtttgat   2459 tagaatcagc ctcaagagct ggcacatgct tgtgaacttg tgctttcata ttttcctaac   2519 ctgtgtggtc tttgtgggag gaataaccca gactaggaat gccagcatct gccaagcagt   2579
```

FIG. 2D

```
tgggataatt cttcactatt ccacccttgc cacagtacta tgggtaggag tgacagctcg 2639
aaatatctac aaacaagtca ctaaaaaagc taaaagatgc caggatcctg atgaaccacc 2699
acctccacca agaccaatgc tcagatttta cctgattggt ggtggtatcc ccatcattgt 2759
ttgcggcata actgcagcag cgaacattaa gaattacggc agtcggccaa acgcacccta 2819
ttgctggatg gcatgggaac cctccttggg agccttctat gggccagcca gcttcatcac 2879
ttttgtaaac tgcatgtact ttctgagcat atttattcag ttgaaaagac accctgagcg 2939
caaatatgag cttaaggagc ccacggagga gcaacagaga ttggcagcca atgaaaatgg 2999
cgaaataaat catcaggatt caatgtcttt gtctctgatt tctacatcag ccttggaaaa 3059
tgagcacact tttcattctc agctcttggg ggccagcctt actttgctct tatatgttgc 3119
actgtggatg tttggggctt tggctgtttc tttgtattac cctttggact tggtttttag 3179
cttcgttttt ggagccacaa gtttaagctt cagtgcgttc ttcatggtcc accattgtgt 3239
taatagggag gatgttagac ttgcgtggat catgacttgc tgcccaggac ggagctcgta 3299
ttcagtgcaa gtcaacgtcc agccccccaa ctctaatggg acgaatggag aggcacccaa 3359
atgccccaat agcagtgcgg agtcttcatg cacaaacaaa agtgcttcaa gcttcaaaaa 3419
ttcctcccag ggctgcaaat taacaaactt gcaggcggct gcagctcagt gccatgccaa 3479
ttctttacct ttgaactcca cccctcagct tgataatagt ctgacagaac attcaatgga 3539
caatgatatt aaaatgcacg tggcgccttt agaagttcag tttcgaacaa atgtgcactc 3599
aagccgccac cataaaaaca gaagtaaagg acaccgggca agccgactca cagtcctgag 3659
agaatatgcc tacgatgtcc caacgagcgt ggaaggaagc gtgcagaacg gcttacctaa 3719
aagccggctg gcaataacg aaggacactc gaggagccga agagcttatt tagcctacag 3779
agagagacag tacaacccac cccagcaaga cagcagcgat gcttgtagca cacttcccaa 3839
aagtagcaga aattttgaaa agccagtttc aaccactagt aaaaaagatg cgttaaggaa 3899
gccagctgtg gttgaacttg aaaatcagca aaaatcttat ggcctcaact tggccattca 3959
gaatggacca attaaaagca atgggcagga gggacccttg ctcggtaccg atagcactgg 4019
caatgttagg actggattat ggaaacacga aactactgtg taacattgct gggcttccta 4079
ggcagaaatt catataaact gtgatactca cattccttga agctatgagc atttaaaaac 4139
tgtttacagc caccataggg attcaaaaga atttggaata aactttgaag ttttggattt 4199
tacttatttt tatccccaaa ttgttgctat tttttaggat ctgaaacaaa atctttctaa 4259
aacattgttt tagttgtcaa agcaccaaca ggacattttg ggat           4303
```

FIG. 3A

```
  3 QGNASKKVEIVVLETSASYCPAERVANNRGDFRWPRTLAGITAYQSCLQY  52
    .||  .: |:|||||.|| ||| ||| ||:||||||||||||||  | .
330 RGNNTRTVDIVVLESSAQYCPPERVVNNKGDFRWPRTLAGITAYLQCTRN 379

53 PFTS.VPLGGGAPGTRASRRCDRAGRWEPGDYSHCLYTNDITRVLYTFVL 101
    | :  |       :| |||||  | |    ||| | | ||:||||| |
380 THGSGIYPGNPQDERKAWRRCDRGGFWADDDYSRCQYANDVTRVLYMFNQ 429

102 MPINASNALTLAHQLRVYTAEAASFSDMMDVVYVAQMIQKFLGYV..DQI 149
    ||:| .||.  | ||  || |||.||| |||::||:||:||   :   :.
430 MPLNLTNAVATARQLLAYTVEAANFSDKMDVIFVAEMIEKFGRFTKEEKS 479

150 KELVEVMVDMASNLMLVDEHLLWLAQREDKACSRIVGALERIGGAALSPH 199
    ||| :||||.|||:|| || .||||||||:||||||| ||||||  |:||    |.
480 KELGDVMVDIASNIMLADERVLWLAQREAKACSRIVQCLQRIATYRLAGG 529

200 AQHISVNARNVALEAYLIKPHSYVGLTCTAFQRREGGVPGTRPGSPGQNP 249
    |   |  . |:||||||.||   : |:|||  || :       |   |.
530 AHVYSTYSPNIALEAYVIKSTGFTGMTCTVFQ.KVAASDRTGLSDYGRR. 577

250 PPEPEPPADQQLRFRCTTGRPNVSLSSFHIKNSVALASIQLPPSLFS.SL 298
    :||     |.|| ||  |:|         ||  :||.: ||||||||||
578 ..DPEGNLDKQLSFKCNVSN...TFSSLALKNTIVEASIQLPPSLFSPKQ 622

299 PAALAPPVPPDCTLQLLVFRNGRLFHSHSNTSRPGAAGPGKRRGVATPVI 348
    |  |        |||: ||||:||  . |..     |  |||| | ||||
623 KRELRPTDDSLYKLQLIAFRNGKLFPATGNST..NLADDGKRRTVVTPVI 670

349 FAGTSGCGVGNLTEPVAVSLRHWAEGAEPVAAWWSQEGPGEAGGWTSEGC 398
    |   |       || |.||  | ||: ||| |   :       |||  |:||
671 LTKIDGVNVDTHHIPVNVTLRRIAHGADAVAARWDFDLLNGQGGWKSDGC 720

399 QLRSSQPNVSALHCQHLGNVAVLMELSAFPREVGGAGAGLHPVVYPCTAL 448
    :    |  |::. :  |   | ||||:|.         |   ||||||    :
721 HILYSDENITTIQCYSLSNYAVLMDLTGSELYTQAASL.HPVVYTTAII 769

449 LLLCLFATIITYILNHSSIRVSRKGWHMLLNLCFHIAMTSAVFAGGITLT 498
    ||||| | |:.||  .|| ||:| |  ||||.|||||| :|  ||  |||| |
770 LLLCLLAVIVSYIYHHSLIRISLKSWHMLVNLCFHIFLTCVVFVGGITQT 819

499 NYQMVCQAVGITLHYSSLSTLLWMGVKARVLHKELTWRAPPPQEGDPALP 548
    :||||||  ||||.|.|.||.|| ||  ::|:.|  :|  |: |    |
820 RNASICQAVGIILHYSTLATVLWVGVTARNIYKQVTKKAKRCQDPDEPPP 869
```

FIG. 3B

```
 549 TPSPMLR........................CWLVWRPSLGA  566
     | ||||                          ||: | |||||
 870 PPRPMLRFYLIGGGIPIIVCGITAAANIKNYGSRPNAPYCWMAWEPSLGA  919

567 FYIPVALILLITWIYFLCAGLRLRGPLAQNPKAGNSRASLEAGEELRGST  616
     ||| . | : .|||  :.|:   ..|.   :  |.   |  .
 920 FYGPASFITFVNCMYFLSIFIQLK....RHPE...RKYELKEPTEEQQRL  962

617 RLRGSGPL.LSDSGSLLATGSARVGTPGPPEDGDSLYSPGVQLGALVTTH  665
      .| :   || ||    ...       |.  .:|    ||| .|
 963 AANENGEINHQDSMSLSLISTSAL......ENEHTFHSQ..LLGASLTL.  1003

666 FLYLAMWACGALAVSQRWLPRVVCSCLYGVAASALGLFVFTHHCARRRDV  715
     ||.|:| ||||||  :   .| | .:|  . .   |    ||| | ||
1004 LLYVALWMFGALAVSLYYPLDLVFSFVFGATSLSFSAFFVVHHCVNREDV  1053

716 RASW.RACCPPASPAAPHA...PPRALPAAAEDGSPVFGEGPPSLKSSPS  761
      .|   |||  | .      ||.        |           |  .. |
1054 RLAWIMTCCPGRSSYSVQVNVQPPNSNGTNGE.APKCPNSSAESSCTNKS  1102

762 GSSGHPLALGPCKLTNLQLAQSQVCEAGA..AAGGEGEPEPAGTRGNL...  807
     ||   . |  |||||||| | .| | | .   : :.   | .  .:
1103 ASSFKNSSQG.CKLTNLQAAAAQ.CHANSLPLNSTPQLDNSLTEHSMDND  1150

808 ..AHRHPNNVH.....HGRRAHKSRAKGHRAGEACGKNRLKALRGGAAGA  850
       | | |        |    | | ||.|.|||||   .|| ||    |
1151 IKMHVAPLEVQFRTNVHSSRHHKNRSKGHRA......SRLTVLR...EYA  1191

851 LELLSSESGSLHNSPTDSYLGSSR...NSPGAGLQLEGEPMLTPSEGSDT  897
     :.  .|   ||. |      |  ||..    | | |           |: |
1192 YDVPTSVEGSVQNGLPKSRLGNNEGHSRSRRAYLAYRERQYNPPQQDSSD  1241

898 SAAPLSEAGRAGQR...RSASRDSLKGGGALEKESHRRSYPLNAASLNGA  944
     . | .. |  ::   .. :|.|:   .| |. .:|| || |   ||
1242 ACSTLPKSSRNFEKPVSTTSKKDALRKPAVVELENQQKSYGLNLAIQNGP  1291

945 PKGGKYDDVTLMGAEVASGGCMKTGLWKSETTV  977
     |    :    |:|  :   | |  .:||||| ||||
1292 IKSNGQEG.PLLGTD..STGNVRTGLWKHETTV  1321
```

TUMOR ENDOTHELIAL MARKER 5α MOLECULES AND USES THEREOF

This application is a division of U.S. application Ser. No. 10/271,697, filed Oct. 15, 2002, issued as U.S. Pat. No. 7,771,965, which claims the benefit of priority from U.S. Provisional Application No. 60/329,223, filed on Oct. 12, 2001, the disclosure of each of which is explicitly incorporated by reference herein.

FIELD OF THE INVENTION

The present invention relates to Tumor Endothelial Marker 5α (TEM5α) polypeptides and nucleic acid molecules encoding the same. The invention also relates to selective binding agents, vectors, host cells, and methods for producing TEM5α polypeptides. The invention further relates to pharmaceutical compositions and methods for the diagnosis, treatment, amelioration, or prevention of diseases, disorders, and conditions associated with TEM5α polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

SUMMARY OF THE INVENTION

The present invention relates to novel TEM5α nucleic acid molecules and encoded polypeptides.

The invention provides for an isolated nucleic acid molecule comprising a nucleotide sequence:

(a) as set forth in either SEQ ID NO: 1 or SEQ ID NO: 3;

(b) encoding the polypeptide as set forth in either SEQ ID NO: 2 or SEQ ID NO: 4;

(c) that hybridizes under at least moderately stringent conditions to the complement of the nucleotide sequence of either (a) or (b), wherein the nucleic acid molecule encodes a polypeptide having an activity of the polypeptide set forth in either SEQ ID NO: 2 or SEQ ID NO: 4; or (d) complementary to the nucleotide sequence of any of (a)-(c).

The invention also provides for an isolated nucleic acid molecule comprising:

(a) a nucleotide sequence encoding a polypeptide that is at least about 70 percent identical to the polypeptide as set forth in either SEQ ID NO: 2 or SEQ ID NO: 4, wherein the encoded polypeptide has an activity of the polypeptide set forth in either SEQ ID NO: 2 or SEQ ID NO: 4;

(b) a nucleotide sequence encoding an allelic variant or splice variant of the nucleotide sequence as set forth in either SEQ ID NO: 1 or SEQ ID NO: 3 or the nucleotide sequence of (a);

(c) a region of the nucleotide sequence of either SEQ ID NO: 1 or SEQ ID NO: 3 or the nucleotide sequence of either (a) or (b), encoding a polypeptide fragment of at least about 25 amino acid residues, wherein the polypeptide fragment has an activity of the polypeptide as set forth in either SEQ ID NO: 2 or SEQ ID NO: 4, or is antigenic;

(d) a region of the nucleotide sequence of either SEQ ID NO: 1 or SEQ ID NO: 3 or the nucleotide sequence of any of (a)-(c) comprising a fragment of at least about 16 nucleotides;

(e) a nucleotide sequence that hybridizes under at least moderately stringent conditions to the complement of the nucleotide sequence of any of (a)-(d), wherein the nucleic acid molecule encodes a polypeptide having an activity of the polypeptide set forth in either SEQ ID NO: 2 or SEQ ID NO: 4; or (f) a nucleotide sequence complementary to the nucleotide sequence of any of (a)-(e).

The invention further provides for an isolated nucleic acid molecule comprising a nucleotide sequence:

(a) encoding a polypeptide as set forth in either SEQ ID NO: 2 or SEQ ID NO: 4 with at least one conservative amino acid substitution, wherein the encoded polypeptide has an activity of the polypeptide set forth in either SEQ ID NO: 2 or SEQ ID NO: 4;

(b) encoding a polypeptide as set forth in either SEQ ID NO: 2 or SEQ ID NO: 4 with at least one amino acid insertion, wherein the encoded polypeptide has an activity of the polypeptide set forth in either SEQ ID NO: 2 or SEQ ID NO: 4;

(c) encoding a polypeptide as set forth in either SEQ ID NO: 2 or SEQ ID NO: 4 with at least one amino acid deletion, wherein the encoded polypeptide has an activity of the polypeptide set forth in either SEQ ID NO: 2 or SEQ ID NO: 4;

(d) encoding a polypeptide as set forth in either SEQ ID NO: 2 or SEQ ID NO: 4 that has a C- and/or N-terminal truncation, wherein the encoded polypeptide has an activity of the polypeptide set forth in either SEQ ID NO: 2 or SEQ ID NO: 4;

(e) encoding a polypeptide as set forth in either SEQ ID NO: 2 or SEQ ID NO: 4 with at least one modification that is an amino acid substitution, amino acid insertion, amino acid deletion, C-terminal truncation, or N-terminal truncation, wherein the encoded polypeptide has an activity of the polypeptide set forth in either SEQ ID NO: 2 or SEQ ID NO: 4;

(f) of any of (a)-(e) comprising a fragment of at least about 16 nucleotides;

(g) that hybridizes under at least moderately stringent conditions to the complement of the nucleotide sequence of any of (a)-(f), wherein the nucleic acid molecule encodes a polypeptide having an activity of the polypeptide set forth in either SEQ ID NO: 2 or SEQ ID NO: 4; or (h) complementary to the nucleotide sequence of any of (a)-(g).

The present invention provides for an isolated polypeptide comprising the amino acid sequence set forth in either SEQ ID NO: 2 or SEQ ID NO: 4.

The invention also provides for an isolated polypeptide comprising:

(a) an amino acid sequence for an ortholog of either SEQ ID NO: 2 or SEQ ID NO: 4;

(b) an amino acid sequence that is at least about 70 percent identical to the amino acid sequence of either SEQ ID NO: 2 or SEQ ID NO: 4, wherein the polypeptide has an activity of the polypeptide set forth in either SEQ ID NO: 2 or SEQ ID NO: 4;

(c) a fragment of the amino acid sequence set forth in either SEQ ID NO: 2 or SEQ ID NO: 4 comprising at least about 25 amino acid residues, wherein the fragment has an activity of the polypeptide set forth in either SEQ ID NO: 2 or SEQ ID NO: 4, or is antigenic; or (d) an amino acid sequence for an allelic variant or splice variant of the amino acid sequence as set forth in either SEQ ID NO: 2 or SEQ ID NO: 4, or the amino acid sequence of either (a) or (b).

The invention further provides for an isolated polypeptide comprising an amino acid sequence as set forth in either SEQ ID NO: 2 or SEQ ID NO: 4:

(a) with at least one conservative amino acid substitution;
(b) with at least one amino acid insertion;
(c) with at least one amino acid deletion;
(d) that has a C- and/or N-terminal truncation; or
(e) with at least one modification that is an amino acid substitution, amino acid insertion, amino acid deletion, C-terminal truncation, or N-terminal truncation;

wherein the polypeptide has an activity of the polypeptide set forth in either SEQ ID NO: 2 or SEQ ID NO: 4.

Also provided are fusion polypeptides comprising TEM5α amino acid sequences.

The present invention also provides for an expression vector comprising the isolated nucleic acid molecules as set forth herein, recombinant host cells comprising the recombinant nucleic acid molecules as set forth herein, and a method of producing a TEM5α polypeptide comprising culturing the host cells and optionally isolating the polypeptide so produced.

A transgenic non-human animal comprising a nucleic acid molecule encoding a TEM5α polypeptide is also encompassed by the invention. The TEM5α nucleic acid molecules are introduced into the animal in a manner that allows expression and increased levels of a TEM5α polypeptide, which may include increased circulating levels. Alternatively, the TEM5α nucleic acid molecules are introduced into the animal in a manner that prevents expression of endogenous TEM5α polypeptide (i.e., generates a transgenic animal possessing a TEM5α polypeptide gene knockout). The transgenic non-human animal is preferably a mammal, and more preferably a rodent, such as a rat or a mouse.

Also provided are derivatives of the TEM5α polypeptides of the present invention.

Additionally provided are selective binding agents such as antibodies and peptides capable of specifically binding the TEM5α polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The TEM5α polypeptides and nucleic acid molecules of the present invention may be used to treat, prevent, ameliorate, and/or detect diseases and disorders, including those recited herein.

The present invention also provides a method of assaying test molecules to identify a test molecule that binds to a TEM5α polypeptide. The method comprises contacting a TEM5α polypeptide with a test molecule to determine the extent of binding of the test molecule to the polypeptide. The method further comprises determining whether such test molecules are agonists or antagonists of a TEM5α polypeptide. The present invention further provides a method of testing the impact of molecules on the expression of TEM5α polypeptide or on the activity of TEM5α polypeptide.

Methods of regulating expression and modulating (i.e., increasing or decreasing) levels of a TEM5α polypeptide are also encompassed by the invention. One method comprises administering to an animal a nucleic acid molecule encoding a TEM5α polypeptide. In another method, a nucleic acid molecule comprising elements that regulate or modulate the expression of a TEM5α polypeptide may be administered. Examples of these methods include gene therapy, cell therapy, and anti-sense therapy as further described herein.

In another aspect of the present invention, TEM5α polypeptides can be used for identifying ligands thereof. Various forms of "expression cloning" have been used for cloning ligands for receptors (See, e.g., Davis et al., 1996, *Cell*, 87:1161-69). These and other TEM5α ligand cloning experiments are described in greater detail herein. Isolation of the TEM5α ligand(s) allows for the identification or development of novel agonists and/or antagonists of the TEM5α signaling pathway. Such agonists and antagonists include TEM5α ligand(s), anti-TEM5α ligand antibodies and derivatives thereof, small molecules, or antisense oligonucleotides, any of which can be used for potentially treating one or more diseases or disorders, including those recited herein.

BRIEF DESCRIPTION OF THE FIGURES

FIGS. 1A-1G show the nucleotide sequence of the human TEM5α gene (SEQ ID NO: 1) and the deduced amino acid sequence of human TEM5α polypeptide (SEQ ID NO: 2);

FIGS. 2A-2D show a nucleotide sequence (SEQ ID NO: 3) encoding soluble form of human TEM5α polypeptide (SEQ ID NO: 4);

FIGS. 3A-3B show an amino acid sequence alignment of human TEM5 polypeptide (upper sequence; SEQ ID NO: 5) and human TEM5α polypeptide (lower sequence; SEQ ID NO: 2);

FIG. 4A) and the soluble form of the human TEM5α polypeptide (SEQ ID NO: 4; FIG. 4B), as indicated following a BLAST analysis of the amino acid sequences against the Conserved Domain Database.

DETAILED DESCRIPTION OF THE INVENTION

Figure 4A:
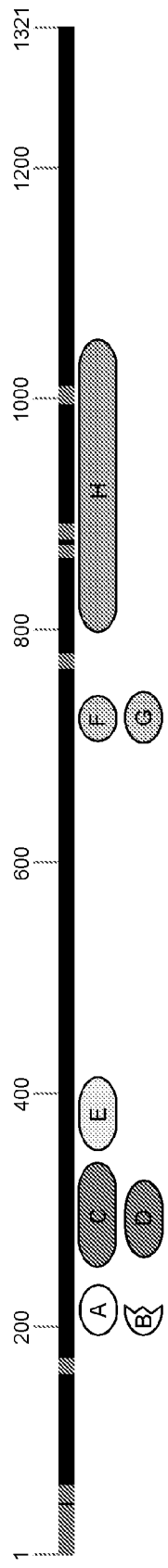
FIGS. 4A-4B illustrate the locations of several conserved domains possessed by the human TEM5α polypeptide (SEQ ID NO: 2.

The section headings used herein are for organizational purposes only and are not to be construed as limiting the subject matter described. All references cited in this application are expressly incorporated by reference herein.

DEFINITIONS

The terms "TEM5α gene" or "TEM5α nucleic acid molecule" or "TEM5α polynucleotide" refer to a nucleic acid molecule comprising or consisting of a nucleotide sequence as set forth in either SEQ ID NO: 1 or SEQ ID NO: 3, a nucleotide sequence encoding the polypeptide as set forth in either SEQ ID NO: 2 or SEQ ID NO: 4, and nucleic acid molecules as defined herein.

The term "TEM5α polypeptide allelic variant" refers to one of several possible naturally occurring alternate forms of a gene occupying a given locus on a chromosome of an organism or a population of organisms.

The term "TEM5α polypeptide splice variant" refers to a nucleic acid molecule, usually RNA, which is generated by alternative processing of intron sequences in an RNA transcript of TEM5α polypeptide amino acid sequence as set forth in either SEQ ID NO: 2 or SEQ ID NO: 4.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl)uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "TEM5α polypeptide" refers to a polypeptide comprising the amino acid sequence of either SEQ ID NO: 2 or SEQ ID NO: 4 and related polypeptides. Related polypeptides include TEM5α polypeptide fragments, TEM5α polypeptide orthologs, TEM5α polypeptide variants, and TEM5α polypeptide derivatives, which possess at least one activity of the polypeptide as set forth in either SEQ ID NO: 2 or SEQ ID NO: 4. TEM5α polypeptides may be mature polypeptides, as defined herein, and may or may not have an amino-terminal methionine residue, depending on the method by which they are prepared.

The term "TEM5α polypeptide fragment" refers to a polypeptide that comprises a truncation at the amino-terminus (with or without a leader sequence) and/or a truncation at the carboxyl-terminus of the polypeptide as set forth in either SEQ ID NO: 2 or SEQ ID NO: 4. The term "TEM5α polypeptide fragment" also refers to amino-terminal and/or carboxyl-terminal truncations of TEM5α polypeptide orthologs, TEM5α polypeptide derivatives, or TEM5α polypeptide variants, or to amino-terminal and/or carboxyl-terminal truncations of the polypeptides encoded by TEM5α polypeptide allelic variants or TEM5α polypeptide splice variants. TEM5α polypeptide fragments may result from alternative RNA splicing or from in vivo protease activity. Membrane-bound forms of a TEM5α polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids, or more than about 200 amino acids. Such TEM5α polypeptide fragments may optionally comprise an amino-terminal methionine residue. It will be appreciated that such fragments can be used, for example, to generate antibodies to TEM5α polypeptides.

The term "TEM5α polypeptide ortholog" refers to a polypeptide from another species that corresponds to TEM5α polypeptide amino acid sequence as set forth in either SEQ ID NO: 2 or SEQ ID NO: 4. For example, mouse and human TEM5α polypeptides are considered orthologs of each other.

The term "TEM5α polypeptide variants" refers to TEM5α polypeptides comprising amino acid sequences having one or more amino acid sequence substitutions, deletions (such as internal deletions and/or TEM5α polypeptide fragments), and/or additions (such as internal additions and/or TEM5α fusion polypeptides) as compared to the TEM5α polypeptide amino acid sequence set forth in either SEQ ID NO: 2 or SEQ ID NO: 4 (with or without a leader sequence). Variants may be naturally occurring (e.g., TEM5α polypeptide allelic variants, TEM5α polypeptide orthologs, and TEM5α polypeptide splice variants) or artificially constructed. Such TEM5α polypeptide variants may be prepared from the corresponding nucleic acid molecules having a DNA sequence that varies accordingly from the DNA sequence as set forth in either SEQ ID NO: 1 or SEQ ID NO: 3. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "TEM5α polypeptide derivatives" refers to the polypeptide as set forth in either SEQ ID NO: 2 or SEQ ID NO: 4, TEM5α polypeptide fragments, TEM5α polypeptide orthologs, or TEM5α polypeptide variants, as defined herein, that have been chemically modified. The term "TEM5α polypeptide derivatives" also refers to the polypeptides encoded by TEM5α polypeptide allelic variants or TEM5α polypeptide splice variants, as defined herein, that have been chemically modified.

The term "mature TEM5α polypeptide" refers to a TEM5α polypeptide lacking a leader sequence. A mature TEM5α polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like.

The term "TEM5α fusion polypeptide" refers to a fusion of one or more amino acids (such as a heterologous protein or peptide) at the amino- or carboxyl-terminus of the polypeptide as set forth in either SEQ ID NO: 2 or SEQ ID NO: 4, TEM5α polypeptide fragments, TEM5α polypeptide orthologs, TEM5α polypeptide variants, or TEM5α derivatives, as defined herein. The term "TEM5α fusion polypeptide" also refers to a fusion of one or more amino acids at the amino- or carboxyl-terminus of the polypeptide encoded by TEM5α polypeptide allelic variants or TEM5α polypeptide splice variants, as defined herein.

The term "biologically active TEM5α polypeptides" refers to TEM5α polypeptides having at least one activity characteristic of the polypeptide comprising the amino acid sequence of either SEQ ID NO: 2 or SEQ ID NO: 4. In addition, a TEM5α polypeptide may be active as an immunogen; that is, the TEM5α polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man. When used in connection with nucleotides, the terms "naturally occurring" or "native" refer to the bases adenine (A), cytosine (C), guanine (G), thymine (T), and uracil (U). When used in connection with amino acids, the terms "naturally occurring" and "native" refer to the 20 amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y).

The terms "effective amount" and "therapeutically effective amount" each refer to the amount of a TEM5α polypeptide or TEM5α nucleic acid molecule used to support an observable level of one or more biological activities of the TEM5α polypeptides as set forth herein.

The term "pharmaceutically acceptable carrier" or "physiologically acceptable carrier" as used herein refers to one or more formulation materials suitable for accomplishing or enhancing the delivery of the TEM5α polypeptide, TEM5α nucleic acid molecule, or TEM5α selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a TEM5α polypeptide. As used herein, the terms, "specific" and "specificity" refer to the ability of the selective binding agents to bind to human TEM5α polypeptides and not to bind to human non-TEM5α polypeptides. It will be appreciated, however, that the selective binding agents may also bind orthologs of the polypeptide as set forth in either SEQ ID NO: 2 or SEQ ID NO: 4, that is, interspecies versions thereof, such as mouse and rat TEM5α polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of either SEQ ID NO: 1 or SEQ ID NO: 3, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide as set forth in either SEQ ID NO: 2 or SEQ ID NO: 4. Such related TEM5α polypeptides may comprise, for example, an addition and/or a deletion of one or more N-linked or O-linked glycosylation sites or an addition and/or a deletion of one or more cysteine residues.

Related nucleic acid molecules also include fragments of TEM5α nucleic acid molecules which encode a polypeptide of at least about 25 contiguous amino acids, or about 50 amino acids, or about 75 amino acids, or about 100 amino acids, or about 150 amino acids, or about 200 amino acids, or more than about 200 amino acid residues of the TEM5α polypeptide of either SEQ ID NO: 2 or SEQ ID NO: 4.

In addition, related TEM5α nucleic acid molecules also include those molecules which comprise nucleotide sequences which hybridize under moderately or highly stringent conditions as defined herein with the fully complementary sequence of the TEM5α nucleic acid molecule of either SEQ ID NO: 1 or SEQ ID NO: 3, or of a molecule encoding a polypeptide, which polypeptide comprises the amino acid sequence as shown in either SEQ ID NO: 2 or SEQ ID NO: 4, or of a nucleic acid fragment as defined herein, or of a nucleic acid fragment encoding a polypeptide as defined herein. Hybridization probes may be prepared using the TEM5α sequences provided herein to screen cDNA, genomic or synthetic DNA libraries for related sequences. Regions of the DNA and/or amino acid sequence of TEM5α polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°\ C.)=81.5+16.6(\log [Na+])+0.41(\%\ G+C)-600/N-0.72(\%\ \text{formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$Tm$=2° C. per $A$-$T$ base pair+4° C. per $G$-$C$ base pair

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in either SEQ ID NO: 1 or SEQ ID NO: 3. In preferred embodiments, the nucleotide sequences are about 75 percent, or about 80 percent, or about 85 percent, or about 90 percent, or about 95, 96, 97, 98, or 99 percent identical to the nucleotide sequence as shown in either SEQ ID NO: 1 or SEQ ID NO: 3. Related nucleic acid molecules encode polypeptides possessing at least one activity of the polypeptide set forth in either SEQ ID NO: 2 or SEQ ID NO: 4.

Differences in the nucleic acid sequence may result in conservative and/or non-conservative modifications of the amino acid sequence relative to the amino acid sequence of either SEQ ID NO: 2 or SEQ ID NO: 4.

Conservative modifications to the amino acid sequence of either SEQ ID NO: 2 or SEQ ID NO: 4 (and the corresponding modifications to the encoding nucleotides) will produce a polypeptide having functional and chemical characteristics similar to those of TEM5α polypeptides. In contrast, substantial modifications in the functional and/or chemical characteristics of TEM5α polypeptides may be accomplished by selecting substitutions in the amino acid sequence of either SEQ ID NO: 2 or SEQ ID NO: 4 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human TEM5α polypeptide that are homologous with non-human TEM5α polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the TEM5α polypeptide, or to increase or decrease the affinity of the TEM5α polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |

TABLE I-continued

Amino Acid Substitutions

| Original Residues | Exemplary Substitutions | Preferred Substitutions |
|---|---|---|
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in either SEQ ID NO: 2 or SEQ ID NO: 4 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a TEM5α polypeptide to such similar polypeptides. With such a comparison, one can identify residues and portions of the molecules that are conserved among similar polypeptides. It will be appreciated that changes in areas of the TEM5α molecule that are not conserved relative to such similar polypeptides would be less likely to adversely affect the biological activity and/or structure of a TEM5α polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a TEM5α polypeptide that correspond to amino acid residues that are important for activity or structure in similar polypeptides. One skilled in the art may opt for chemically similar amino acid substitutions for such predicted important amino acid residues of TEM5α polypeptides.

One skilled in the art can also analyze the three-dimensional structure and amino acid sequence in relation to that structure in similar polypeptides. In view of such information, one skilled in the art may predict the alignment of amino acid residues of TEM5α polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, Curr. Opin. Biotechnol. 7:422-27; Chou et al., 1974, Biochemistry 13:222-45; Chou et al., 1974, Biochemistry 113:211-22; Chou et al., 1978, Adv. Enzymol. Relat. Areas Mol. Biol. 47:45-48; Chou et al., 1978, Ann. Rev. Biochem. 47:251-276; and Chou et al., 1979, Biophys. J. 26:367-84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, Nucleic Acids Res. 27:244-47. It has been suggested that there are a limited number of folds in a given polypeptide or protein and that once a critical number of structures have been resolved, structural prediction will become dramatically more accurate (Brenner et al., 1997, Curr. Opin. Struct. Biol. 7:369-76).

Additional methods of predicting secondary structure include "threading" (Jones, 1997, Curr. Opin. Struct. Biol. 7:377-87; Sippl et al., 1996, Structure 4:15-19), "profile analysis" (Bowie et al., 1991, Science, 253:164-70; Gribskov et al., 1990, Methods Enzymol. 183:146-59; Gribskov et al., 1987, Proc. Nat. Acad. Sci. U.S.A. 84:4355-58), and "evolutionary linkage" (See Holm et al., supra, and Brenner et al., supra).

Preferred TEM5α polypeptide variants include glycosylation variants wherein the number and/or type of glycosylation sites have been altered compared to the amino acid sequence set forth in either SEQ ID NO: 2 or SEQ ID NO: 4. In one embodiment, TEM5α polypeptide variants comprise a greater or a lesser number of N-linked glycosylation sites than the amino acid sequence set forth in either SEQ ID NO: 2 or SEQ ID NO: 4. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred TEM5α variants include cysteine variants, wherein one or more cysteine residues are deleted or substituted with another amino acid (e.g., serine) as compared to the amino acid sequence set forth in either SEQ ID NO: 2 or SEQ ID NO: 4. Cysteine variants are useful when TEM5α polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, TEM5α polypeptide variants comprise an amino acid sequence as set forth in either SEQ ID NO: 2 or SEQ ID NO: 4 with at least one amino acid insertion and wherein the polypeptide has an activity of the polypeptide set forth in either SEQ ID NO: 2 or SEQ ID NO: 4, or an amino acid sequence encoding a polypeptide as set forth in either SEQ ID NO: 2 or SEQ ID NO: 4 with at least one amino acid deletion and wherein the polypeptide has an activity of the polypeptide set forth in either SEQ ID NO: 2 or SEQ ID NO: 4. TEM5α polypeptide variants also comprise an amino acid sequence as set forth in either SEQ ID NO: 2 or SEQ ID NO: 4 wherein the polypeptide has a carboxyl- and/or amino-terminal truncation and further wherein the polypeptide has an activity of the polypeptide set forth in either SEQ ID NO: 2 or SEQ ID NO: 4. TEM5α polypeptide variants further comprise an amino acid sequence as set forth in either SEQ ID NO: 2 or SEQ ID NO: 4 with at least one modification that is an amino acid substitution, amino acid insertion, amino acid deletion, carboxyl-terminal truncation, or amino-terminal truncation, and wherein the polypeptide has an activity of the polypeptide set forth in either SEQ ID NO: 2 or SEQ ID NO: 4.

In further embodiments, TEM5α polypeptide variants comprise an amino acid sequence that is at least about 70 percent identical to the amino acid sequence as set forth in either SEQ ID NO: 2 or SEQ ID NO: 4. In preferred embodiments, TEM5α polypeptide variants comprise an amino acid sequence that is at least about 75 percent, or about 80 percent, or about 85 percent, or about 90 percent, or about 95, 96, 97, 98, or 99 percent identical to the amino acid sequence as set forth in either SEQ ID NO: 2 or SEQ ID NO: 4. TEM5α polypeptide variants possess at least one activity of the polypeptide set forth in either SEQ ID NO: 2 or SEQ ID NO: 4.

In addition, the polypeptide comprising the amino acid sequence of either SEQ ID NO: 2 or SEQ ID NO: 4, or other TEM5α polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a TEM5α fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in either SEQ ID NO: 2 or SEQ ID NO: 4, or other TEM5α polypeptide.

Fusions can be made either at the amino-terminus or at the carboxyl-terminus of the polypeptide comprising the amino acid sequence set forth in either SEQ ID NO: 2 or SEQ ID NO: 4, or other TEM5α polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of either SEQ ID NO: 2 or SEQ ID NO: 4, or other TEM5α polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, *J. Immunol.* 154: 5590-600 |
| IgG1 | TNF receptor | septic shock | Fisher et al., 1996, *N. Engl. J. Med.* 334: 1697-1702; Van Zee et al., 1996, *J. Immunol.* 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, *Nature* 337: 525-31 |
| IgG1, IgG3 | N-terminus of IL-2 | anti-cancer, antiviral | Harvill et al., 1995, *Immunotech.* 1: 95-105 |
| IgG1 | C-terminus of OPG | osteoarthritis; bone density | International Pub. No. WO 97/23614 |
| IgG1 | N-terminus of leptin | anti-obesity | International Pub. No. WO 98/28427 |
| Human Ig Cγ1 | CTLA-4 | autoimmune disorders | Linsley, 1991, *J. Exp. Med.*, 174: 561-69 |

In one example, a human IgG hinge, CH2, and CH3 region may be fused at either the amino-terminus or carboxyl-terminus of the TEM5α polypeptides using methods known to the skilled artisan. In another example, a human IgG hinge, CH2, and CH3 region may be fused at either the amino-terminus or carboxyl-terminus of a TEM5α polypeptide fragment (e.g., the predicted extracellular portion of TEM5α polypeptide).

The resulting TEM5α fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Useful modifications of protein therapeutic agents by fusion with the "Fc" domain of an antibody are discussed in detail in U.S. patent application Ser. No. 09/428,082 (International Pub. No. WO 99/25044), which is hereby incorporated by reference in its entirety. That patent application discusses linkage to a "vehicle" such as polyethylene gycol (PEG), dextran, or an Fc region.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heijne, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978) (PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:
Algorithm: Needleman and Wunsch, 1970, *J. Mol. Biol.* 48:443-53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a TEM5α polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a TEM5α polypeptide has been identified from one species, all or a portion of that gene may be used as a probe to identify orthologs or related genes from the same species. The probes or primers may be used to screen cDNA libraries from various tissue sources believed to express the TEM5α polypeptide. In addition, part or all of a nucleic acid molecule having the sequence as set forth in either SEQ ID NO: 1 or SEQ ID NO: 3 may be used to screen a genomic library to identify and isolate a gene encoding the amino acid sequence of a TEM5α polypeptide. Typically, conditions of moderate or high stringency will be employed for screening to minimize the number of false positives obtained from the screening.

Nucleic acid molecules encoding the amino acid sequence of TEM5α polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a TEM5α polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a TEM5α polypeptide can be inserted into an expression vector. By introducing the expression vector into an appropriate host, the encoded TEM5α polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA encoding the amino acid sequence of a TEM5α polypeptide, are then added to the cDNA along with a polymerase such as Taq polymerase, and the polymerase amplifies the cDNA region between the two primers.

Another means of preparing a nucleic acid molecule encoding the amino acid sequence of a TEM5α polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a TEM5α polypeptide will be several hundred nucleotides in length. Nucleic acids larger than about 100 nucleotides can be synthesized as several fragments using these methods. The fragments can then be ligated together to form the full-length nucleotide sequence of a TEM5α gene. Usually, the DNA fragment encoding the amino-terminus of the polypeptide will have an ATG, which encodes a methionine residue. This methionine may or may not be present on the mature form of the TEM5α polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a TEM5α polypeptide in a given host cell. Particular codon alterations will depend upon the TEM5α polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "Drosophila_high.cod," "Human_high.cod," "Maize_high.cod," and "Yeast_high.cod."

In some cases, it may be desirable to prepare nucleic acid molecules encoding TEM5α polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a TEM5α polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a TEM5α polypeptide may be amplified/expressed in prokaryotic, yeast, insect (baculovirus systems) and/or eukaryotic host cells. Selection of the host cell will depend in part on whether a TEM5α polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the TEM5α polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the TEM5α polypeptide from the host cell. Affinity purification can be accomplished, for example, by column chromatography using antibodies against the tag as an affinity matrix. Optionally, the tag can subsequently be removed from the purified TEM5α polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences that normally function to regulate TEM5α polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the TEM5α gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a TEM5α polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a TEM5α polypeptide. As a result, increased quantities of TEM5α polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a TEM5α polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a TEM5α polypeptide out of the host cell. Typically, a nucleotide sequence encoding the signal sequence is positioned in the coding region of a TEM5α nucleic acid molecule, or directly at the 5' end of a TEM5α polypeptide coding region. Many signal sequences have been identified, and any of those that are functional in the selected host cell may be used in conjunction with a TEM5α nucleic acid molecule. Therefore, a signal sequence may be homologous (naturally occurring) or heterologous to the TEM5α nucleic acid molecule. Additionally, a signal sequence may be chemically synthesized using methods described herein. In most cases, the secretion of a TEM5α polypeptide from the host cell via the presence of a signal peptide will result in the removal of the signal peptide from the secreted TEM5α polypeptide. The signal sequence may be a component of the vector, or it may be a part of a TEM5α nucleic acid molecule that is inserted into the vector.

Included within the scope of this invention is the use of either a nucleotide sequence encoding a native TEM5α polypeptide signal sequence joined to a TEM5α polypeptide coding region or a nucleotide sequence encoding a heterologous signal sequence joined to a TEM5α polypeptide coding region. The heterologous signal sequence selected should be one that is recognized and processed, i.e., cleaved by a signal peptidase, by the host cell. For prokaryotic host cells that do not recognize and process the native TEM5α polypeptide signal sequence, the signal sequence is substituted by a prokaryotic signal sequence selected, for example, from the group of the alkaline phosphatase, penicillinase, or heat-stable enterotoxin II leaders. For yeast secretion, the native TEM5α polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired TEM5α polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the TEM5α gene especially where the gene used is a full-length genomic sequence or a fragment thereof. Where the intron is not naturally occurring within the gene (as for most cDNAs), the intron may be obtained from another source. The position of the intron with respect to flanking sequences and the TEM5α gene is generally important, as the intron must be transcribed to be effective. Thus, when a TEM5α cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the TEM5α polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding TEM5α polypeptide by removing the promoter from the source DNA by restriction enzyme digestion and inserting the desired promoter sequence into the vector. The native TEM5α promoter sequence may be used to direct amplification and/or expression of a TEM5α nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling TEM5α gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the met-allothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234:1372-78).

An enhancer sequence may be inserted into the vector to increase the transcription of a DNA encoding a TEM5α polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a TEM5α nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pCRII, pCR3, and pcDNA3.1 (Invitrogen, Carlsbad, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (International Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid; Stratagene Cloning Systems; La Jolla Calif.), PCR cloning plasmids designed for cloning Taq-amplified PCR products (e.g., TOPO™ TA Cloning® Kit, PCR2.1® plasmid derivatives; Invitrogen), and mammalian, yeast or virus vectors such as a baculovirus expression system (pBacPAK plasmid derivatives; Clontech; Palo Alto, Calif.).

After the vector has been constructed and a nucleic acid molecule encoding a TEM5α polypeptide has been inserted into the proper site of the vector, the completed vector may be inserted into a suitable host cell for amplification and/or polypeptide expression. The transformation of an expression vector for a TEM5α polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a TEM5α polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated TEM5α polypeptides. For example, one may use a transgenic milk-producing animal (a cow or goat, for example) and obtain the present glycosylated polypeptide in the animal milk. One may also use plants to produce TEM5α polypeptides, however, in general, the glycosylation occurring in plants is different from that produced in mammalian cells, and may result in a glycosylated product which is not suitable for human therapeutic use.

Polypeptide Production

Host cells comprising a TEM5α polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a TEM5α polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a TEM5α polypeptide has been designed to be secreted from the host cells, the majority of polypeptide may be found in the cell culture medium. If however, the TEM5α polypeptide is not secreted from the host cells, it will be present in the cytoplasm and/or the nucleus (for eukaryotic host cells) or in the cytosol (for gram-negative bacteria host cells).

For a TEM5α polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a TEM5α polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized TEM5α polypeptide can then be analyzed using gel electrophoresis, immunoprecipitation, or the like. If it is desired to isolate the TEM5α polypeptide, isolation may be accomplished using standard methods such as those described herein and in Marston et al., 1990, *Meth. Enz.*, 182:264-75.

In some cases, a TEM5α polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol (DTT)/dithiane DTT, and 2-2-mercaptoethanol (bME)/dithio-b (ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a TEM5α polypeptide, then the polypeptide will be found primarily in the supernatant after centrifugation of the cell homogenate. The polypeptide may be further isolated from the supernatant using methods such as those described herein.

The purification of a TEM5α polypeptide from solution can be accomplished using a variety of techniques. If the polypeptide has been synthesized such that it contains a tag such as Hexahistidine (TEM5α polypeptide/hexaHis) or other small peptide such as FLAG (Eastman Kodak Co., New Haven, Conn.) or myc (Invitrogen) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of TEM5α polypeptide/polyHis. See, e.g., *Current Protocols in Molecular Biology* §10.11.8 (Ausubel et al., eds., Green Publishers Inc. and Wiley and Sons 1993).

Additionally, TEM5α polypeptides may be purified through the use of a monoclonal antibody that is capable of specifically recognizing and binding to a TEM5α polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

TEM5α polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized TEM5α polypeptides may be oxidized using methods set forth in these references to form disulfide bridges. Chemically synthesized TEM5α polypeptides are expected to have comparable biological activity to the corresponding TEM5α polypeptides produced recombinantly or purified from natural sources, and thus may be used interchangeably with a recombinant or natural TEM5α polypeptide.

Another means of obtaining TEM5α polypeptide is via purification from biological samples such as source tissues and/or fluids in which the TEM5α polypeptide is naturally found. Such purification can be conducted using methods for protein purification as described herein. The presence of the TEM5α polypeptide during purification may be monitored, for example, using an antibody prepared against recombinantly produced TEM5α polypeptide or peptide fragments thereof.

A number of additional methods for producing nucleic acids and polypeptides are known in the art, and the methods can be used to produce polypeptides having specificity for TEM5α polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central pre-selected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in International Pub. No. WO99/15650, filed by Athersys, Inc. Known as "Random Activation of Gene Expression for Gene Discovery" (RAGE-GD), the process involves the activation of endogenous gene expression or over-expression of a gene by in situ recombination methods.

For example, expression of an endogenous gene is activated or increased by integrating a regulatory sequence into the target cell that is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive TEM5α polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more TEM5α polypeptides. Suitable selective binding agents include, but are not limited to, antibodies and derivatives thereof, polypeptides, and small molecules. Suitable selective binding agents may be prepared using methods known in the art. An exemplary TEM5α polypeptide selective binding agent of the present invention is capable of binding a certain portion of the TEM5α polypeptide thereby inhibiting the binding of the polypeptide to a TEM5α polypeptide receptor.

Selective binding agents such as antibodies and antibody fragments that bind TEM5α polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the TEM5α polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a TEM5α polypeptide generally are produced in animals (e.g., rabbits or mice) by means of multiple subcutaneous or intraperitoneal injections of TEM5α polypeptide and an adjuvant. It may be useful to conjugate a TEM5α polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-TEM5α antibody titer.

Monoclonal antibodies directed toward TEM5α polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with TEM5α polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind TEM5α polypeptides. Using transgenic animals (e.g., mice) that are capable of producing a repertoire of human antibodies in the absence of endogenous immunoglobulin production such antibodies are produced by immunization with a TEM5α polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is animals having less than the full complement of modifications, are then crossbred to obtain an animal having all of the desired immune system modifications. When administered an immunogen, these transgenic animals produce antibodies with human (rather than, e.g., murine) amino acid sequences, including variable regions that are immunospecific for these antigens. See International Pub. Nos. WO 96/33735 and WO 94/02602. Additional methods are described in U.S. Pat. No. 5,545,807, International Pub. Nos. WO 91/10741 and WO 90/04036, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in International Pub. No. WO 99/10494, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-TEM5α antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of TEM5α polypeptides. The antibodies will bind TEM5α polypeptides with an affinity that is appropriate for the assay method being employed.

For diagnostic applications, in certain embodiments, anti-TEM5α antibodies may be labeled with a detectable moiety. The detectable moiety can be any one that is capable of producing, either directly or indirectly, a detectable signal. For example, the detectable moiety may be a radioisotope, such as $^3H$, $^{14}C$, $^{32}P$, $^{35}S$, $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a TEM5α polypeptide, or an immunologically reactive portion thereof) to compete with the test sample analyte (an TEM5α polypeptide) for binding with a limited amount of anti-TEM5α antibody. The amount of a TEM5α polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-TEM5α antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a TEM5α polypeptide. In one embodiment, antagonist antibodies of the invention are antibodies or binding fragments thereof which are capable of specifically binding to a TEM5α polypeptide and which are capable of inhibiting or eliminating the functional activity of a TEM5α polypeptide in vivo or in vitro. In preferred embodiments, the selective binding agent, e.g., an antagonist antibody, will inhibit the functional activity of a TEM5α polypeptide by at least about 50%, and preferably by at least about 80%. In another embodiment, the selective binding agent may be an anti-TEM5α polypeptide antibody that is capable of interacting with a TEM5α polypeptide binding partner (a ligand or receptor) thereby inhibiting or eliminating TEM5α polypeptide activity in vitro or in vivo. Selective binding agents, including agonist and antagonist anti-TEM5α polypeptide antibodies, are identified by screening assays that are well known in the art.

The invention also relates to a kit comprising TEM5α selective binding agents (such as antibodies) and other reagents useful for detecting TEM5α polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the TEM5α molecules of the invention, including, but not limited to: the identification and validation of TEM5α disease-related genes as targets for therapeutics; molecular toxicology of related TEM5α molecules and inhibitors thereof; stratification of populations and generation of surrogate markers for clinical trials; and enhancing related TEM5α polypeptide small molecule drug discovery by aiding in the identification of selective compounds in high throughput screens.

Chemical Derivatives

Chemically modified derivatives of TEM5α polypeptides may be prepared by one skilled in the art, given the disclosures described herein. TEM5α polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of either SEQ ID NO: 2 or SEQ ID NO: 4, or other TEM5α polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that may be used to prepare covalently attached TEM5α polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of either SEQ ID NO: 2 or SEQ ID NO: 4, or other TEM5α polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the TEM5α polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, TEM5α polypeptides may be chemically coupled to biotin. The biotin/TEM5α polypeptide molecules are then allowed to bind to avidin, resulting in tetravalent avidin/biotin/TEM5α polypeptide molecules. TEM5α polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present TEM5α polypeptide derivatives include those described herein for TEM5α polypeptides. However, the TEM5α polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native TEM5α polypeptide have been disrupted (i.e., "knocked out") such that the level of expression of TEM5α polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a TEM5α gene for that animal or a heterologous TEM5α gene is over-expressed by the animal, thereby creating a "transgenic" animal. Such transgenic animals may be prepared using well known methods such as those described in U.S. Pat. No. 5,489,743 and International Pub. No. WO 94/28122.

The present invention further includes non-human animals in which the promoter for one or more of the TEM5α polypeptides of the present invention is either activated or inactivated (e.g., by using homologous recombination methods) to alter the level of expression of one or more of the native TEM5α polypeptides.

These non-human animals may be used for drug candidate screening. In such screening, the impact of a drug candidate on the animal may be measured. For example, drug candidates may decrease or increase the expression of the TEM5α gene. In certain embodiments, the amount of TEM5α polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of TEM5α Polypeptide Activity

In some situations, it may be desirable to identify molecules that are modulators, i.e., agonists or antagonists, of the activity of TEM5α polypeptide. Natural or synthetic molecules that modulate TEM5α polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a TEM5α polypeptide. Most commonly, a test molecule will interact directly with a TEM5α polypeptide. However, it is also contemplated that a test molecule may also modulate TEM5α polypeptide activity indirectly, such as by affecting TEM5α gene expression, or by binding to a TEM5α polypeptide binding partner (e.g., receptor or ligand). In one embodiment, a test molecule will bind to a TEM5α polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with TEM5α polypeptides are encompassed by the present invention. In certain embodiments, a TEM5α polypeptide is incubated with a test molecule under conditions that permit the interaction of the test molecule with a TEM5α polypeptide, and the extent of the interaction is measured. The test molecule can be screened in a substantially purified form or in a crude mixture.

In certain embodiments, a TEM5α polypeptide agonist or antagonist may be a protein, peptide, carbohydrate, lipid, or small molecular weight molecule that interacts with TEM5α polypeptide to regulate its activity. Molecules which regulate TEM5α polypeptide expression include nucleic acids which are complementary to nucleic acids encoding a TEM5α polypeptide, or are complementary to nucleic acids sequences which direct or control the expression of TEM5α polypeptide, and which act as anti-sense regulators of expression.

Once a test molecule has been identified as interacting with a TEM5α polypeptide, the molecule may be further evaluated for its ability to increase or decrease TEM5α polypeptide activity. The measurement of the interaction of a test molecule with TEM5α polypeptide may be carried out in several formats, including cell-based binding assays, membrane binding assays, solution-phase assays, and immunoassays. In general, a test molecule is incubated with a TEM5α polypeptide for a specified period of time, and TEM5α polypeptide activity is determined by one or more assays for measuring biological activity.

The interaction of test molecules with TEM5α polypeptides may also be assayed directly using polyclonal or monoclonal antibodies in an immunoassay. Alternatively, modified forms of TEM5α polypeptides containing epitope tags as described herein may be used in solution and immunoassays.

In the event that TEM5α polypeptides display biological activity through an interaction with a binding partner (e.g., a receptor or a ligand), a variety of in vitro assays may be used to measure the binding of a TEM5α polypeptide to the corresponding binding partner (such as a selective binding agent, receptor, or ligand). These assays may be used to screen test molecules for their ability to increase or decrease the rate and/or the extent of binding of a TEM5α polypeptide to its binding partner. In one assay, a TEM5α polypeptide is immobilized in the wells of a microtiter plate. Radiolabeled TEM5α polypeptide binding partner (for example, iodinated TEM5α polypeptide binding partner) and a test molecule can then be added either one at a time (in either order) or simultaneously to the wells. After incubation, the wells can be washed and counted for radioactivity, using a scintillation counter, to determine the extent to which the binding partner bound to the TEM5α polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing TEM5α polypeptide binding partner to the microtiter plate wells, incubating with the test molecule and radiolabeled TEM5α polypeptide, and determining the extent of TEM5α polypeptide binding. See, e.g., *Current Protocols in Molecular Biology, chap.* 18 (Ausubel et al., eds., Green Publishers Inc. and Wiley and Sons 1995).

As an alternative to radiolabeling, a TEM5α polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a TEM5α polypeptide or to a TEM5α polypeptide binding partner, and which is conjugated to biotin, may also be used for purposes of detection following incubation of the complex with enzyme-linked streptavidin linked to AP or HRP.

A TEM5α polypeptide or a TEM5α polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a TEM5α polypeptide and its binding partner can be assessed using the methods described herein. Alternatively, the substrate-protein complex can be immobilized in a column with the test molecule and complementary protein passing through the column. The formation of a complex between a TEM5α polypeptide and its binding partner can then be assessed using any of the techniques described herein (e.g., radiolabelling or antibody binding).

Another in vitro assay that is useful for identifying a test molecule that increases or decreases the formation of a complex between a TEM5α polypeptide binding protein and a TEM5α polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either TEM5α polypeptide or a TEM5α polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a TEM5α polypeptide and a TEM5α polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a TEM5α polypeptide and TEM5α polypeptide binding partner. The assays may be automated to screen compounds generated in phage display, synthetic peptide, and chemical synthesis libraries.

Compounds which increase or decrease the formation of a complex between a TEM5α polypeptide and a TEM5α polypeptide binding partner may also be screened in cell culture using cells and cell lines expressing either TEM5α polypeptide or TEM5α polypeptide binding partner. Cells and cell lines may be obtained from any mammal, but preferably will be from human or other primate, canine, or rodent sources. The binding of a TEM5α polypeptide to cells expressing TEM5α polypeptide binding partner at the surface is evaluated in the presence or absence of test molecules, and the extent of binding may be determined by, for example, flow cytometry using a biotinylated antibody to a TEM5α polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the TEM5α gene. In certain embodiments, the amount of TEM5α polypeptide or a TEM5α polypeptide fragment that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 6) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 7), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a TEM5α antagonist (such as an anti-TEM5α selective binding agent, small molecule, soluble receptor, or antisense oligonucleotide) can be administered intracellularly to inhibit the activity of a TEM5α molecule. As used herein, the term "TEM5α molecule" refers to both TEM5α nucleic acid molecules and TEM5α polypeptides as defined herein. Where desired, the TEM5α protein itself may also be internally administered to a cell using these procedures. See also, Straus, 1999, *Science* 285:1466-67.

Cell Source Identification Using TEM5α Polypeptide

In accordance with certain embodiments of the invention, it may be useful to be able to determine the source of a certain cell type associated with a TEM5α polypeptide. For example, it may be useful to determine the origin of a disease or pathological condition as an aid in selecting an appropriate therapy. In certain embodiments, nucleic acids encoding a TEM5α polypeptide can be used as a probe to identify cells described herein by screening the nucleic acids of the cells with such a probe. In other embodiments, one may use anti-TEM5α polypeptide antibodies to test for the presence of TEM5α polypeptide in cells, and thus, determine if such cells are of the types described herein.

TEM5α Polypeptide Compositions and Administration

Therapeutic compositions are within the scope of the present invention. Such TEM5α polypeptide pharmaceutical compositions may comprise a therapeutically effective amount of a TEM5α polypeptide or a TEM5α nucleic acid molecule in admixture with a pharmaceutically or physiologically acceptable formulation agent selected for suitability with the mode of administration. Pharmaceutical compositions may comprise a therapeutically effective amount of one or more TEM5α polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the TEM5α molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, TEM5α polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the TEM5α polypeptide product may be formulated as a lyophilizate using appropriate excipients such as sucrose.

The TEM5α polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired TEM5α molecule in a pharmaceutically acceptable vehicle. A particularly suitable vehicle for parenteral injection is sterile distilled water in which a TEM5α molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, TEM5α polypeptide may be formulated as a dry powder for inhalation. TEM5α polypeptide or nucleic acid molecule inhalation solutions may also be formulated with a propellant for aerosol delivery. In yet another embodiment, solutions may be nebulized. Pulmonary administration is further described in International Pub. No. WO 94/20069, which describes the pulmonary delivery of chemically modified proteins.

It is also contemplated that certain formulations may be administered orally. In one embodiment of the present invention, TEM5α polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the TEM5α polypeptide. Diluents, flavorings, low melting point waxes, vegetable oils, lubricants, suspending agents, tablet disintegrating agents, and binders may also be employed.

Another pharmaceutical composition may involve an effective quantity of TEM5α polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional TEM5α polypeptide pharmaceutical compositions will be evident to those skilled in the art, including formulations involving TEM5α polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., International Pub. No. WO 93/15722, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The TEM5α pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a TEM5α pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the TEM5α molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the TEM5α molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use TEM5α polypeptide pharmaceutical compositions in an ex vivo manner. In such instances, cells, tissues, or organs that have been removed from the patient are exposed to TEM5α polypeptide pharmaceutical compositions after which the cells, tissues, or organs are subsequently implanted back into the patient.

In other cases, a TEM5α polypeptide can be delivered by implanting certain cells that have been genetically engineered, using methods such as those described herein, to express and secrete the TEM5α polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more TEM5α polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent TEM5α gene, or an under-expressed gene, and thereby produce a cell which expresses therapeutically efficacious amounts of TEM5α polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; and International Pub. Nos. WO 91/09955 and WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a TEM5α polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired TEM5α polypeptide. The control element controls a portion of the DNA present in the host cell genome. Thus, the expression of the desired TEM5α polypeptide may be achieved not by transfection of DNA that encodes the TEM5α gene itself, but rather by the use of targeting DNA (containing regions of homology with the endogenous gene of interest) coupled with DNA regulatory segments that provide the endogenous gene sequence with recognizable signals for transcription of a TEM5α gene.

In an exemplary method, the expression of a desired targeted gene in a cell (i.e., a desired endogenous cellular gene) is altered via homologous recombination into the cellular genome at a preselected site, by the introduction of DNA that includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, TEM5α polypeptide production from a cell's endogenous TEM5α gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic TEM5α polypeptide coding region. A plasmid containing a recombination site homologous to the site that was placed just upstream of the genomic TEM5α polypeptide coding region is introduced into the modified cell line along with the appropriate recombinase enzyme. This recombinase causes the plasmid to integrate, via the plasmid's recombination site, into the recombination site located just upstream of the genomic TEM5α polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased TEM5α polypeptide production from the cell's endogenous TEM5α gene.

A further method to use the cell line in which the site specific recombination sequence had been placed just upstream of the cell's endogenous genomic TEM5α polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol.*, 225:890-900) that would create a new or modified transcriptional unit resulting in de novo or increased TEM5α polypeptide production from the cell's endogenous TEM5α gene.

An additional approach for increasing, or causing, the expression of TEM5α polypeptide from a cell's endogenous TEM5α gene involves increasing, or causing, the expression of a gene or genes (e.g., transcription factors) and/or decreasing the expression of a gene or genes (e.g., transcriptional repressors) in a manner which results in de novo or increased TEM5α polypeptide production from the cell's endogenous TEM5α gene. This method includes the introduction of a non-naturally occurring polypeptide (e.g., a polypeptide comprising a site specific DNA binding domain fused to a transcriptional factor domain) into the cell such that de novo or increased TEM5α polypeptide production from the cell's endogenous TEM5α gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of TEM5α polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a TEM5α polypeptide, which nucleotides may be used as targeting sequences.

TEM5α polypeptide cell therapy, e.g., the implantation of cells producing TEM5α polypeptides, is also contemplated. This embodiment involves implanting cells capable of synthesizing and secreting a biologically active form of TEM5α polypeptide. Such TEM5α polypeptide-producing cells can be cells that are natural producers of TEM5α polypeptides or may be recombinant cells whose ability to produce TEM5α polypeptides has been augmented by transformation with a gene encoding the desired TEM5α polypeptide or with a gene augmenting the expression of TEM5α polypeptide. Such a modification may be accomplished by means of a vector suitable for delivering the gene as well as promoting its expression and secretion. In order to minimize a potential immunological reaction in patients being administered a TEM5α polypeptide, as may occur with the administration of a polypeptide of a foreign species, it is preferred that the natural cells producing TEM5α polypeptide be of human origin and produce human TEM5α polypeptide. Likewise, it is preferred that the recombinant cells producing TEM5α polypeptide be transformed with an expression vector containing a gene encoding a human TEM5α polypeptide.

Implanted cells may be encapsulated to avoid the infiltration of surrounding tissue. Human or non-human animal cells may be implanted in patients in biocompatible, semipermeable polymeric enclosures or membranes that allow the release of TEM5α polypeptide, but that prevent the destruction of the cells by the patient's immune system or by other detrimental factors from the surrounding tissue. Alternatively, the patient's own cells, transformed to produce TEM5α polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (International Pub. No. WO 95/05452 and International Pub. No. WO 95/05452) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in International Pub. No. WO 91/10425 (Aebischer et al.). See also, International Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of TEM5α polypeptides is also envisioned. One example of a gene therapy technique is to use the TEM5α gene (either genomic DNA, cDNA, and/or synthetic DNA) encoding a TEM5α polypeptide that may be operably linked to a constitutive or inducible promoter to form a "gene therapy DNA construct." The promoter may be homologous or heterologous to the endogenous TEM5α gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the TEM5α gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see International Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and International Pub. Nos. WO 96/40911 and WO 97/10337.

Yet another control system uses ecdysone (a fruit fly steroid hormone) that binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and International Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding TEM5α polypeptide into cells via local injection of a TEM5α nucleic acid molecule or by other appropriate viral or non-viral delivery vectors. Hefti 1994, *Neurobiology* 25:1418-35. For example, a nucleic acid molecule encoding a TEM5α polypeptide may be contained in an adeno-associated virus (AAV) vector for delivery to the targeted cells (see, e.g., International Pub. Nos. WO 95/34670 and WO 95/34670). The recombinant AAV genome typically contains AAV inverted terminal repeats flanking a DNA sequence encoding a TEM5α polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. Nos. 5,631,236 (involving adenoviral vectors), 5,672,510 (involving retroviral vectors), 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. Nos. 4,970,154 (involving electroporation techniques), 5,679,559 (describing a lipoprotein-containing system for gene delivery), 5,676,954 (involving liposome carriers), 5,593,875 (describing methods for calcium phosphate transfection), and 4,945,050 (describing a process wherein biologically active particles are propelled at cells at a speed whereby the particles penetrate the surface of the cells and become incorporated into the interior of the cells), and International Pub. No. WO 96/40958 (involving nuclear ligands).

It is also contemplated that TEM5α gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous TEM5α polypeptide expression in a cell via gene therapy is to insert one or more enhancer elements into the TEM5α polypeptide promoter, where the enhancer elements can serve to increase transcriptional activity of the TEM5α gene. The enhancer elements used will be selected based on the tissue in which one desires to activate the gene—enhancer elements known to confer promoter activation in that tissue will be selected. For example, if a gene encoding a TEM5α polypeptide is to be "turned on" in T-cells, the lck promoter enhancer element may be used. Here, the functional portion of the transcriptional element to be added may be inserted into a fragment of DNA containing the TEM5α polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease TEM5α polypeptide expression by modifying the nucleotide sequence of the endogenous promoter. Such modification is typically accomplished via homologous recombination methods. For example, a DNA molecule containing all or a portion of the promoter of the TEM5α gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding TEM5α gene. The deletion of the TATA box or the transcription activator binding site in the promoter may be accomplished by generating a DNA construct comprising all or the relevant portion of the TEM5α polypeptide promoter (from the same or a related species as the TEM5α gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

TEM5α nucleic acid molecules, polypeptides, and agonists and antagonists thereof can be used to treat, diagnose, ameliorate, or prevent a number of diseases, disorders, or conditions, including those recited herein.

TEM5α polypeptide agonists and antagonists include those molecules which regulate TEM5α polypeptide activity and either increase or decrease at least one activity of the mature form of the TEM5α polypeptide. Agonists or antagonists may be co-factors, such as a protein, peptide, carbohydrate, lipid, or small molecular weight molecule, which interact with TEM5α polypeptide and thereby regulate its activity. Potential polypeptide agonists or antagonists include antibodies that react with either soluble or membrane-bound forms of TEM5α polypeptides that comprise part or all of the extracellular domains of the said proteins. Molecules that regulate TEM5α polypeptide expression typically include nucleic acids encoding TEM5α polypeptide that can act as anti-sense regulators of expression.

Since TEM5α polypeptide expression has been detected in the lung, TEM5α nucleic acid molecules, polypeptides, agonists and antagonists thereof (including, but not limited to, anti-TEM5α selective binding agents) may be useful for the treatment or diagnosis of diseases involving the lung. Examples of such diseases include, but are not limited to, asthma, bronchospasm, and acute respiratory distress syndrome. Other diseases associated with the lung are encompassed within the scope of the invention.

Since TEM5α polypeptide expression has been detected in the heart, TEM5α nucleic acid molecules, polypeptides, agonists and antagonists thereof (including, but not limited to, anti-TEM5α selective binding agents) may be useful for the treatment or diagnosis of diseases involving the heart. Examples of such diseases include, but are not limited to, arrhythmias, angina, hypertension, myocardial infarction and congestive heart failure. Other diseases associated with the heart are encompassed within the scope of the invention.

Since TEM5α polypeptide expression has been detected in the kidney, TEM5α nucleic acid molecules, polypeptides, agonists and antagonists thereof (including, but not limited to, anti-TEM5α selective binding agents) may be useful for the treatment or diagnosis of diseases involving the kidney. Examples of such diseases include, but are not limited to, polycystic kidney disease, and acute renal failure. Other diseases associated with the kidney are encompassed within the scope of the invention.

Since TEM5α polypeptide expression has been detected in the pancreas, TEM5α nucleic acid molecules, polypeptides, agonists and antagonists thereof (including, but not limited to, anti-TEM5α selective binding agents) may be useful for the treatment or diagnosis of diseases involving the pancreas. Examples of such diseases include, but are not limited to, diabetes, obesity, and gastro intestinal failure. Other diseases associated with the pancreas are encompassed within the scope of the invention.

Expression of TEM5 has been detected in the endothelial compartment of blood vessels in colorectal tumor (St. Croix et al., 2000, *Science* 289:1197-202). Therefore, TEM5α polypeptides may play a role in the regulation of angiogenesis in primary and metastatic tumors. Accordingly, TEM5α nucleic acid molecules, polypeptides, agonists and antagonists thereof (including, but not limited to, anti-TEM5α selective binding agents) may be useful as surrogate markers for the treatment or diagnosis of cancer diseases. Examples of such diseases include, but are not limited to, colorectal cancer, breast cancer, lung cancer, stomach cancer, pancreatic cancer and liver cancer. Other primary and metastatic cancer diseases are encompassed within the scope of the invention.

TEM5α polypeptides may also play a role in the control of angiogenesis in inflammatory diseases. Accordingly, TEM5α nucleic acid molecules, polypeptides, agonists and antagonists thereof (including, but not limited to, anti-TEM5α selective binding agents) may be useful for the treatment or diagnosis of inflammatory diseases. Examples of such diseases include, but are not limited to, rheumatoid arthritis and inflammatory bowel disease. Other inflammatory diseases are encompassed within the scope of the invention.

Agonists or antagonists of TEM5α polypeptide function may be used (simultaneously or sequentially) in combination with one or more cytokines, growth factors, antibiotics, anti-inflammatories, and/or chemotherapeutic agents as is appropriate for the condition being treated.

Other diseases or disorders caused by or mediated by undesirable levels of TEM5α polypeptides are encompassed within the scope of the invention. Undesirable levels include excessive levels of TEM5α polypeptides and sub-normal levels of TEM5α polypeptides.

Uses of TEM5α Nucleic Acids and Polypeptides

Nucleic acid molecules of the invention (including those that do not themselves encode biologically active polypeptides) may be used to map the locations of the TEM5α gene and related genes on chromosomes. Mapping may be done by techniques known in the art, such as PCR amplification and in situ hybridization.

TEM5α nucleic acid molecules (including those that do not themselves encode biologically active polypeptides), may be useful as hybridization probes in diagnostic assays to test, either qualitatively or quantitatively, for the presence of a TEM5α nucleic acid molecule in mammalian tissue or bodily fluid samples.

Other methods may also be employed where it is desirable to inhibit the activity of one or more TEM5α polypeptides. Such inhibition may be effected by nucleic acid molecules that are complementary to and hybridize to expression control sequences (triple helix formation) or to TEM5α mRNA. For example, antisense DNA or RNA molecules, which have a sequence that is complementary to at least a portion of a TEM5α gene can be introduced into the cell. Anti-sense probes may be designed by available techniques using the sequence of the TEM5α gene disclosed herein. Typically, each such antisense molecule will be complementary to the start site (5' end) of each selected TEM5α gene. When the antisense molecule then hybridizes to the corresponding TEM5α mRNA, translation of this mRNA is prevented or reduced. Anti-sense inhibitors provide information relating to the decrease or absence of a TEM5α polypeptide in a cell or organism.

Alternatively, gene therapy may be employed to create a dominant-negative inhibitor of one or more TEM5α polypeptides. In this situation, the DNA encoding a mutant polypeptide of each selected TEM5α polypeptide can be prepared and introduced into the cells of a patient using either viral or non-viral methods as described herein. Each such mutant is typically designed to compete with endogenous polypeptide in its biological role.

In addition, a TEM5α polypeptide, whether biologically active or not, may be used as an immunogen, that is, the polypeptide contains at least one epitope to which antibodies may be raised. Selective binding agents that bind to a TEM5α polypeptide (as described herein) may be used for in vivo and in vitro diagnostic purposes, including, but not limited to, use in labeled form to detect the presence of TEM5α polypeptide in a body fluid or cell sample. The antibodies may also be used to prevent, treat, or diagnose a number of diseases and disorders, including those recited herein. The antibodies may bind to a TEM5α polypeptide so as to diminish or block at least one activity characteristic of a TEM5α polypeptide, or may bind to a polypeptide to increase at least one activity characteristic of a TEM5α polypeptide (including by increasing the pharmacokinetics of the TEM5α polypeptide).

TEM5α polypeptides can be used to clone TEM5α ligands using an "expression cloning" strategy. Radiolabeled ($^{125}$Iodine) TEM5α polypeptide or "affinity/activity-tagged" TEM5α polypeptide (such as an Fc fusion or an alkaline phosphatase fusion) can be used in binding assays to identify a cell type, cell line, or tissue that expresses a TEM5α ligand. RNA isolated from such cells or tissues can then be converted to cDNA, cloned into a mammalian expression vector, and transfected into mammalian cells (e.g., COS or 293) to create an expression library. Radiolabeled or tagged TEM5α polypeptide can then be used as an affinity reagent to identify and isolate the subset of cells in this library expressing a TEM5α ligand. DNA is then isolated from these cells and transfected into mammalian cells to create a secondary expression library in which the fraction of cells expressing the TEM5α ligand would be many-fold higher than in the original library. This enrichment process can be repeated iteratively until a single recombinant clone containing the TEM5α ligand is isolated. Isolation of TEM5α ligands is useful for identifying or developing novel agonists and antagonists of the TEM5α signaling pathway. Such agonists and antagonists include TEM5α ligands, anti-TEM5α ligand antibodies, small molecules or antisense oligonucleotides.

The TEM5α nucleic acids of the present invention are also useful tools for isolating the corresponding chromosomal TEM5α polypeptide genes. For example, mouse chromosomal DNA containing TEM5α sequences can be used to construct knockout mice, thereby permitting an examination of the in vivo role for TEM5α polypeptide. The human TEM5α genomic DNA can be used to identify heritable tissue-degenerating diseases.

The following examples are intended for illustration purposes only, and should not be construed as limiting the scope of the invention in any way.

Example 1

Cloning of the Human TEM5α Polypeptide Genes

Generally, materials and methods as described in Sambrook et al. supra were used to clone and analyze the genes encoding human and murine TEM5α polypeptides.

A human TEM5 cDNA sequence was used as a probe to identify sequences corresponding to the murine TEM5α gene in proprietary and public expressed sequence tag (EST) databases. The murine TEM5α sequence was then used as a probe to identify sequences corresponding to several exons of the human TEM5α gene in a proprietary human genomic sequence database. Human TEM5α cDNA sequences were isolated from a human kidney cDNA library panel (OriGene Technologies; Rockville, Md.) by PCR using amplimers derived from the predicted exon sequences of the human TEM5α gene (5'-G-T-G-G-T-G-G-T-T-C-A-T-C-A-G-G-A-T-C-C-3'; SEQ ID NO: 8 and 5'-C-T-T-C-A-C-T-A-T-T-C-C-A-C-C-C-T-T-G-C-3'; SEQ ID NO: 9). After identifying three positive cDNA pools using this first amplimer pair, the full-length coding sequence for the human TEM5α gene was isolated using four amplimer pairs (pair #1: 5'-G-G-G-C-G-G-T-A-G-G-C-G-T-G-T-A-C-G-G-T-G-G-3'; SEQ ID NO: 10 and 5'-G-C-A-T-G-T-C-A-A-C-A-G-C-T-C-C-T-G-C-3'; SEQ ID NO: 11; pair #2: 5'-C-C-A-G-A-C-T-G-A-G-T-A-T-C-T-T-T-T-G-3'; SEQ ID NO: 12 and 5'-G-C-A-A-T-G-C-G-C-T-G-A-A-G-A-C-A-C-T-G-3'; SEQ ID NO: 13; pair #3: 5'-A-G-G-T-G-A-C-G-T-G-A-T-G-G-T-T-G-A-C-3'; SEQ ID NO: 14 and 5'-G-T-G-G-T-G-G-T-T-C-A-T-C-A-G-G-A-T-C-C-3'; SEQ ID NO: 15; pair #4: 5'-G-G-G-A-G-G-G-G-T-C-A-C-A-G-G-G-A-T-G-3', SEQ ID NO: 16 and 5'-C-T-T-C-A-C-T-A-T-T-C-C-A-C-C-C-T-T-G-C-3'; SEQ ID NO: 17). The PCR products generated in this second amplification reaction were subcloned into the pCR 2.1 vector (Invitrogen) and positive clones were sequenced. A consensus sequence for the human TEM5α gene was derived from the sequences obtained for at least three clones.

Sequence analysis of the full-length cDNA for human TEM5α polypeptide indicated that the gene comprises a 3963 bp open reading frame encoding a protein of 1321 amino acids. FIGS. 1A-1G show the nucleotide sequence of the human TEM5α gene and the deduced amino acid sequence of the human TEM5α polypeptide.

One of the three positive pools from the initial library screening was found to comprise a TEM5α nucleic acid sequence containing a 14 base pair insertion between bases 1830 and 1831 of the nucleotide sequence shown in FIGS. 1A-1G. This insertion results in a premature translational stop, forming a short (559 amino acids), soluble form of TEM5α (sTEM5α). FIGS. 2A-2D show the nucleotide sequence and deduced amino acid sequence of sTEM5α polypeptide.

The TEM5α and sTEM5α nucleic acid sequences encode polypeptides that are related to tumor endothelial marker 5 (TEM5) (St. Croix et al., 2000, *Science* 289:1197-202). FIGS. 3A-3B illustrate an amino acid sequence alignment of human TEM5α polypeptide (huTEM5α; SEQ ID NO: 4) and human TEM5. The human TEM5α gene shares a 63.5% similarity with the human TEM5 gene and human TEM5α polypeptide shares a 60% similarity with human TEM5 polypeptide. The structure of both human and mouse TEM5α polypeptide parallels that of TEM5 in that both polypeptides contain a predicted signal peptide sequence in the N-terminus and seven transmembrane domains near the C-terminus, suggesting that TEM5α is a membrane-bound protein. The sTEM5α polypeptide comprises a predicted signal peptide and an extracellular domain, and lacks the seven transmembrane domains.

Figure 4B:
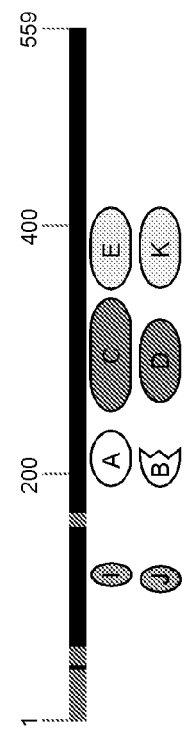

A BLAST analysis of the amino acid sequences for the human TEM5α polypeptide and the soluble form of the human TEM5α polypeptide performed against the Conserved Domain Database (a collection of functional and structural domains derived primarily from the Smart and Pfam databases) indicated that these proteins possess a number of conserved protein domains. Specifically, both the full-length and soluble forms possess a leucine-rich repeat C-terminal (LRRCT) domain (indicated as domains A and B in FIGS. 4A and 4B), an immunoglobulin (Ig) domain (indicated as domains C and D in FIGS. 4A and 4B), and a hormone receptor (HRM) domain (indicated as domain E in FIGS. 4A and 4B and domain K in FIG. 4B). The BLAST analysis also indicated that the human TEM5α polypeptide also possesses a G-protein coupled receptor protelytic site (GPS) domain (indicated as domains F and G in FIG. 4A) and a 7 transmembrane receptor (7tm_2) domain (indicated as domain H in FIG. 4A). The BLAST analysis further indicated that the soluble form of the human TEM5α polypeptide possesses a leucine-rich repeat (LRR) domain (panels I and J in FIG. 4B).

The sequence of the human TEM5α gene was used to search both the CELERA human genomic and GenBank databases. The human TEM5α gene was found to span about 132 kb and consist of 19 exons and 18 introns. Exon 1 of the human TEM5α gene was located in GenBank Accession No. AC093814, and exons 2 through 19 were identified in the CELERA human genomic database. Exon/intron junctions were predicted using Fichant's rule (Fichant, 1992, *Hum. Mol. Genet.* 1:259-67). The location and the numbers of exon/intron junctions for TEM5α are similar to those of TEM5, suggesting that the two genes derive from a common ancestor.

The human TEM5α gene was located in a large contig sequence in the CELERA human genomic database, oriented in an anti-sense direction toward the telomere of the p arm of chromosome 4. This contig sequence also contains the cytosolic β-glucosidase (CBG; GenBANK Accession No. AF323990), peroxisome proliferator-activated receptor γ (PPARGC1, GenBANK Accession No. NM_013261), and SLIT2 (GenBANK Accession No. NM_004787) genes. The human CBG gene is about 158 kb proximal to the human TEM5α gene, and the human PPARGC1 gene is about 1250 kb proximal to the human TEM5α gene. In the distal region, the human SLIT2 gene is about 1890 kb away from the human TEM5α gene. The CBG, PPARGC1, and SLIT2 genes have been mapped to the human chromosome 4p15 region, suggesting that the human TEM5α gene will be located in this region as well.

Example 2

TEM5α mRNA Expression

The expression of human TEM5α was analyzed by PCR using amplimers derived from the predicted exon sequence as described in Example 1 (5'-G-T-G-G-T-G-G-T-T-C-A-T-C-A-G-G-A-T-C-C-3'; SEQ ID NO: 8 and 5'-C-T-T-C-A-C-T-A-T-T-C-C-A-C-C-C-T-T-G-C-3'; SEQ ID NO: 9). The expected PCR product (112 bp) was detected in heart, lung, kidney, pancreas, placenta, brain, skeletal muscle, ovary, liver, prostate, and testis. The expected PCR product was not detected in spleen, thymus, or leukocytes. TEM5 has been shown to be elevated in the endothelial compartment of blood vessels in colorectal tumors. TEM5 (as well as other members of the TEM family) expression has also been shown in sarcomas and in primary cancers of the lung, breast, brain, and pancreas. In addition, TEM expression has been shown in metastatic endothelial tissues.

The expression of TEM5α mRNA is examined by Northern blot analysis. Multiple human tissue northern blots (Clontech) are probed with a suitable restriction fragment isolated from a human TEM5α polypeptide cDNA clone. The probe is labeled with $^{32}$P-dCTP using standard techniques.

Northern blots are prehybridized for 2 hours at 42° C. in hybridization solution (5×SSC, 50% deionized formamide, 5×Denhardt's solution, 0.5% SDS, and 100 mg/ml denatured salmon sperm DNA) and then hybridized at 42° C. overnight in fresh hybridization solution containing 5 ng/ml of the labeled probe. Following hybridization, the filters are washed twice for 10 minutes at room temperature in 2×SSC and 0.1% SDS, and then twice for 30 minutes at 65° C. in 0.1×SSC and 0.1% SDS. The blots are then exposed to autoradiography.

The expression of TEM5α mRNA is localized by in situ hybridization. A panel of normal embryonic and adult mouse tissues is fixed in 4% paraformaldehyde, embedded in paraffin, and sectioned at 5 µm. Sectioned tissues are permeabilized in 0.2 M HCl, digested with Proteinase K, and acetylated with triethanolamine and acetic anhydride. Sections are prehybridized for 1 hour at 60° C. in hybridization solution (300 mM NaCl, 20 mM Tris-HCl, pH 8.0, 5 mM EDTA, 1×Denhardt's solution, 0.2% SDS, 10 mM DTT, 0.25 mg/ml tRNA, 25 µg/ml polyA, 25 µg/ml polyC and 50% formamide) and then hybridized overnight at 60° C. in the same solution containing 10% dextran and $2\times10^4$ cpm/µl of a $^{33}$P-labeled antisense riboprobe complementary to the human TEM5α gene. The riboprobe is obtained by in vitro transcription of a clone containing human TEM5α cDNA sequences using standard techniques.

Following hybridization, sections are rinsed in hybridization solution, treated with RNaseA to digest unhybridized probe, and then washed in 0.1×SSC at 55° C. for 30 minutes. Sections are then immersed in NTB-2 emulsion (Kodak, Rochester, N.Y.), exposed for 3 weeks at 4° C., developed, and counterstained with hematoxylin and eosin. Tissue morphology and hybridization signal are simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymus, prostate, seminal vesicle, and vas deferens in the male), BAT and WAT (subcutaneous, peri-renal), bone (femur), skin, breast, and skeletal muscle.

Example 3

Production of TEM5α Polypeptides

A. Expression of TEM5α Polypeptides in Bacteria

PCR is used to amplify template DNA sequences encoding a TEM5α polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC no. 98113) containing the lux promoter and a gene encoding kanamycin resistance is digested with Bam HI and Nde I for directional cloning of inserted DNA. The ligated mixture is transformed into an E. coli host strain by electroporation and transformants are selected for kanamycin resistance. Plasmid DNA from selected colonies is isolated and subjected to DNA sequencing to confirm the presence of the insert.

Transformed host cells are incubated in 2×YT medium containing 30 µg/mL kanamycin at 30° C. prior to induction. Gene expression is induced by the addition of N-(3-oxohexanoyl)-dl-homoserine lactone to a final concentration of 30 ng/mL followed by incubation at either 30° C. or 37° C. for six hours. The expression of TEM5α polypeptide is evaluated by centrifugation of the culture, resuspension and lysis of the bacterial pellets, and analysis of host cell proteins by SDS-polyacrylamide gel electrophoresis.

Inclusion bodies containing TEM5α polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 mL of a Percoll solution (75% liquid Percoll and 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to E. coli-produced TEM5α polypeptide is excised from the gel, and the N-terminal amino acid sequence is determined essentially as described by Matsudaira et al., 1987, J. Biol. Chem. 262:10-35.

B. Expression of TEM5α Polypeptide in Mammalian Cells

PCR is used to amplify template DNA sequences encoding a TEM5α polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen), that contains an Epstein-Barr virus origin of replication, may be used for the expression of TEM5α polypeptides in 293-EBNA-1 cells. Amplified and gel purified PCR products are ligated into pCEP4 vector and introduced into 293-EBNA cells by lipofection. The transfected cells are selected in 100 µg/mL hygromycin and the resulting drug-resistant cultures are grown to confluence. The cells are then cultured in serum-free media for 72 hours. The conditioned media is removed and TEM5α polypeptide expression is analyzed by SDS-PAGE.

TEM5α polypeptide expression may be detected by silver staining. Alternatively, TEM5α polypeptide is produced as a fusion protein with an epitope tag, such as an IgG constant domain or a FLAG epitope, which may be detected by Western blot analysis using antibodies to the peptide tag.

TEM5α polypeptides may be excised from an SDS-polyacrylamide gel, or TEM5α fusion proteins are purified by affinity chromatography to the epitope tag, and subjected to N-terminal amino acid sequence analysis as described herein.

C. Expression and Purification of TEM5α Polypeptide in Mammalian Cells

TEM5α polypeptide expression constructs are introduced into 293 EBNA or CHO cells using either a lipofection or calcium phosphate protocol.

To conduct functional studies on the TEM5α polypeptides that are produced, large quantities of conditioned media are generated from a pool of hygromycin selected 293 EBNA clones. The cells are cultured in 500 cm Nunc Triple Flasks to 80% confluence before switching to serum free media a week prior to harvesting the media. Conditioned media is harvested and frozen at −20° C. until purification.

Conditioned media is purified by affinity chromatography as described below. The media is thawed and then passed through a 0.2 µm filter. A Protein G column is equilibrated with PBS at pH 7.0, and then loaded with the filtered media. The column is washed with PBS until the absorbance at $A_{280}$ reaches a baseline. TEM5α polypeptide is eluted from the column with 0.1 M Glycine-HCl at pH 2.7 and immediately neutralized with 1 M Tris-HCl at pH 8.5. Fractions containing TEM5α polypeptide are pooled, dialyzed in PBS, and stored at −70° C.

For Factor Xa cleavage of the human TEM5α polypeptide-Fc fusion polypeptide, affinity chromatography-purified protein is dialyzed in 50 mM Tris-HCl, 100 mM NaCl, 2 mM $CaCl_2$ at pH 8.0. The restriction protease Factor Xa is added to the dialyzed protein at 1/100 (w/w) and the sample digested overnight at room temperature.

Example 4

Production of Anti-TEM5α Polypeptide Antibodies

Antibodies to TEM5α polypeptides may be obtained by immunization with purified protein or with TEM5α peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a TEM5α antigen (such as a TEM5α polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 µg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-TEM5α antibody production by ELISA.

Alternative procedures for obtaining anti-TEM5α antibodies may also be employed, such as the immunization of transgenic mice harboring human Ig loci for production of human antibodies, and the screening of synthetic antibody libraries, such as those generated by mutagenesis of an antibody variable domain.

Example 5

Expression of TEM5α Polypeptide in Transgenic Mice

To assess the biological activity of TEM5α polypeptide, a construct encoding a TEM5α polypeptide/Fc fusion protein under the control of a liver specific ApoE promoter is prepared. The delivery of this construct is expected to cause pathological changes that are informative as to the function of TEM5α polypeptide. Similarly, a construct containing the full-length TEM5α polypeptide under the control of the beta actin promoter is prepared. The delivery of this construct is expected to result in ubiquitous expression.

To generate these constructs, PCR is used to amplify template DNA sequences encoding a TEM5α polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified TEM5α polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The TEM5α polypeptide expression vector is purified through two rounds of CsCl density gradient centrifugation, cleaved with a suitable restriction enzyme, and the linearized fragment containing the TEM5α polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (International Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScript™ Preamplification System (Gibco-BRL) as follows. A suitable primer, located in the expression vector sequence and 3' to the TEM5α polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2 U of RNase H for 20 minutes at 37° C. Samples are then amplified by PCR using primers specific for TEM5α polypeptide.

Example 6

Biological Activity of TEM5α Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B-cell and T-cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1\times10^6$ cells from each tissue are then incubated for 10 minutes with 0.5 μg CD16/32(FcγIII/II) Fc block in a 20 μL volume. Samples are then stained for 30 minutes at 2-8° C. in a 100 μL volume of PBS (lacking $Ca^+$ and $Mg^+$), 0.1% bovine serum albumin, and 0.01% sodium azide with 0.5 μg antibody of FITC or PE-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An antibody or fragment thereof that specifically binds an isolated polypeptide comprising: (i) the amino acid sequence of SEQ ID NO: 2; (ii) the amino acid sequence of SEQ ID NO: 4; (iii) the amino acid sequence of SEQ ID NO: 2, further comprising an amino-terminal methionine; or (iv) the amino acid sequence of SEQ ID NO: 4, further comprising an amino-terminal methionine.

2. The antibody or fragment thereof of claim 1, wherein the antibody is a humanized antibody.

3. The antibody or fragment thereof of claim 1, wherein the antibody is a human antibody.

4. The antibody or fragment thereof of claim 1, wherein the antibody is a polyclonal antibody.

5. The antibody or fragment thereof of claim 1, wherein the antibody is a monoclonal antibody.

6. The antibody or fragment thereof of claim 1, wherein the antibody is a chimeric antibody.

7. The antibody or fragment thereof of claim 1, wherein the antibody is a CDR-grafted antibody.

8. The antibody or fragment thereof of claim 1, wherein the fragment is a Fab or F(ab').

9. The antibody or fragment thereof of claim 1, wherein the antibody or fragment thereof is bound to a detectable label.

10. A hybridoma that produces a monoclonal antibody that binds an isolated polypeptide comprising: (i) the amino acid sequence of SEQ ID NO: 2; (ii) the amino acid sequence of SEQ ID NO: 4; (iii) the amino acid sequence of SEQ ID NO: 2, further comprising an amino-terminal methionine; or (iv) the amino acid sequence of SEQ ID NO: 4, further comprising an amino-terminal methionine.

11. A kit for detecting or quantitating the amount of TEM5α polypeptide in a biological sample, comprising the antibody or fragment thereof of claim 1.

* * * * *

SEQUENCE LISTING

<160> NUMBER OF SEQ ID NOS: 17

<210> SEQ ID NO 1
<211> LENGTH: 4536
<212> TYPE: DNA
<213> ORGANISM: Homo sapiens
<220> FEATURE:
<221> NAME/KEY: CDS
<222> LOCATION: (227)..(4189)

<400> SEQUENCE: 1

```
gtagagcggc tgctgggacc catgcggccg tgaccccgg ctccctagag gcccagcgca      60
gccgcagcgg acaaaggagc atgtccgcgc cggggaaggc ccgtcctccg gccgccataa     120
ggctccggtc gccgctgggc ccgcgccgcg ctcctgcccg ccgggctccg gggcggcccg     180
ctaggccagt gcgccgccgc tcgccccgca ggccccggcc cgcagc atg gag cca       235
                                                  Met Glu Pro
                                                    1 ccc gga cgc cgg cgg ggc cgc gcg cag ccg ccg ctg ttg ctg ccg ctc      283
Pro Gly Arg Arg Arg Gly Arg Ala Gln Pro Pro Leu Leu Leu Pro Leu
     5                   10                  15 tcg ctg tta gcg ctg ctc gcg ctg ctg gga ggc ggc ggc ggc ggc ggc      331
Ser Leu Leu Ala Leu Leu Ala Leu Leu Gly Gly Gly Gly Gly Gly Gly
 20                  25                  30                  35 gcc gcg gcg ctg ccc gcc ggc tgc aag cac gat ggg cgg ccc cga ggg      379
Ala Ala Ala Leu Pro Ala Gly Cys Lys His Asp Gly Arg Pro Arg Gly
                 40                  45                  50 gct ggc agg gcg gcg ggc gcc gcc gag ggc aag gtg gtg tgc agc agc      427
Ala Gly Arg Ala Ala Gly Ala Ala Glu Gly Lys Val Val Cys Ser Ser
             55                  60                  65 ctg gaa ctc gcg cag gtc ctg ccc cca gat act ctg ccc aac cgc acg      475
Leu Glu Leu Ala Gln Val Leu Pro Pro Asp Thr Leu Pro Asn Arg Thr
         70                  75                  80 gtc acc ctg att ctg agt aac aat aag ata tcc gag ctg aag aat ggc      523
Val Thr Leu Ile Leu Ser Asn Asn Lys Ile Ser Glu Leu Lys Asn Gly
     85                  90                  95 tca ttt tct ggg tta agt ctc ctt gaa aga ttg gac ctc cga aac aat      571
Ser Phe Ser Gly Leu Ser Leu Leu Glu Arg Leu Asp Leu Arg Asn Asn
100                 105                 110                 115 ctt att agt agt ata gat cca ggt gcc ttc tgg gga ctg tca tct cta      619
Leu Ile Ser Ser Ile Asp Pro Gly Ala Phe Trp Gly Leu Ser Ser Leu
                 120                 125                 130 aaa aga ttg gat ctg aca aac aat cga ata gga tgt ctg aat gca gac      667
Lys Arg Leu Asp Leu Thr Asn Asn Arg Ile Gly Cys Leu Asn Ala Asp
             135                 140                 145
```

-continued

| | | |
|---|---|---|
| ata ttt cga gga ctc acc aat ctg gtt cgg cta aac ctt tcg ggg aat<br>Ile Phe Arg Gly Leu Thr Asn Leu Val Arg Leu Asn Leu Ser Gly Asn<br>150              155              160 | 715 | |
| ttg ttt tct tca tta tct caa gga act ttt gat tat ctt gcg tca tta<br>Leu Phe Ser Ser Leu Ser Gln Gly Thr Phe Asp Tyr Leu Ala Ser Leu<br>165              170              175 | 763 | |
| cgg tct ttg gaa ttc cag act gag tat ctt ttg tgt gac tgt aac ata<br>Arg Ser Leu Glu Phe Gln Thr Glu Tyr Leu Leu Cys Asp Cys Asn Ile<br>180              185              190              195 | 811 | |
| ctg tgg atg cat cgc tgg gta aag gag aag aac atc acg gta cgg gat<br>Leu Trp Met His Arg Trp Val Lys Glu Lys Asn Ile Thr Val Arg Asp<br>              200              205              210 | 859 | |
| acc agg tgt gtt tat cct aag tca ctg cag gcc caa cca gtc aca ggc<br>Thr Arg Cys Val Tyr Pro Lys Ser Leu Gln Ala Gln Pro Val Thr Gly<br>              215              220              225 | 907 | |
| gtg aag cag gag ctg ttg aca tgc gac cct ccg ctt gaa ttg ccg tct<br>Val Lys Gln Glu Leu Leu Thr Cys Asp Pro Pro Leu Glu Leu Pro Ser<br>230              235              240 | 955 | |
| ttc tac atg act cca tct cat cgc caa gtt gtg ttt gaa gga gac agc<br>Phe Tyr Met Thr Pro Ser His Arg Gln Val Val Phe Glu Gly Asp Ser<br>245              250              255 | 1003 | |
| ctt cct ttc cag tgc atg gct tca tat att gat cag gac atg caa gtg<br>Leu Pro Phe Gln Cys Met Ala Ser Tyr Ile Asp Gln Asp Met Gln Val<br>260              265              270              275 | 1051 | |
| ttg tgg tat cag gat ggg aga ata gtt gaa acc gat gaa tcg caa ggt<br>Leu Trp Tyr Gln Asp Gly Arg Ile Val Glu Thr Asp Glu Ser Gln Gly<br>              280              285              290 | 1099 | |
| att ttt gtt gaa aag aac atg att cac aac tgc tcc ttg att gca agt<br>Ile Phe Val Glu Lys Asn Met Ile His Asn Cys Ser Leu Ile Ala Ser<br>              295              300              305 | 1147 | |
| gcc cta acc att tct aat att cag gct gga tct act gga aat tgg ggc<br>Ala Leu Thr Ile Ser Asn Ile Gln Ala Gly Ser Thr Gly Asn Trp Gly<br>              310              315              320 | 1195 | |
| tgt cat gtc cag acc aaa cgt ggg aat aat acg agg act gtg gat att<br>Cys His Val Gln Thr Lys Arg Gly Asn Asn Thr Arg Thr Val Asp Ile<br>325              330              335 | 1243 | |
| gtg gta tta gag agt tct gca cag tac tgt ccg cca gag agg gtg gta<br>Val Val Leu Glu Ser Ser Ala Gln Tyr Cys Pro Pro Glu Arg Val Val<br>340              345              350              355 | 1291 | |
| aac aac aaa ggt gac ttc aga tgg ccc aga aca ttg gca ggc att act<br>Asn Asn Lys Gly Asp Phe Arg Trp Pro Arg Thr Leu Ala Gly Ile Thr<br>              360              365              370 | 1339 | |
| gca tat ctg cag tgt acg cgg aac acc cat ggc agt ggg ata tat ccc<br>Ala Tyr Leu Gln Cys Thr Arg Asn Thr His Gly Ser Gly Ile Tyr Pro<br>              375              380              385 | 1387 | |
| gga aac cca cag gat gag aga aaa gct tgg cgc aga tgt gat aga ggt<br>Gly Asn Pro Gln Asp Glu Arg Lys Ala Trp Arg Arg Cys Asp Arg Gly<br>              390              395              400 | 1435 | |
| ggc ttt tgg gca gat gat gat tat tct cgc tgt cag tat gca aat gat<br>Gly Phe Trp Ala Asp Asp Asp Tyr Ser Arg Cys Gln Tyr Ala Asn Asp<br>405              410              415 | 1483 | |
| gtc act aga gtt ctt tat atg ttt aat cag atg ccc ctc aat ctt acc<br>Val Thr Arg Val Leu Tyr Met Phe Asn Gln Met Pro Leu Asn Leu Thr<br>420              425              430              435 | 1531 | |
| aat gcc gtg gca aca gct cga cag tta ctg gct tac act gtg gaa gca<br>Asn Ala Val Ala Thr Ala Arg Gln Leu Leu Ala Tyr Thr Val Glu Ala<br>              440              445              450 | 1579 | |
| gcc aac ttt tct gac aaa atg gat gtt ata ttt gtg gca gaa atg att<br>Ala Asn Phe Ser Asp Lys Met Asp Val Ile Phe Val Ala Glu Met Ile<br>455              460              465 | 1627 | |

| | |
|---|---|
| gaa aaa ttt gga aga ttt acc aag gag gaa aaa tca aaa gag cta ggt<br>Glu Lys Phe Gly Arg Phe Thr Lys Glu Glu Lys Ser Lys Glu Leu Gly<br>470 475 480 | 1675 |
| gac gtg atg gtt gac att gca agt aac atc atg ttg gct gat gaa cgt<br>Asp Val Met Val Asp Ile Ala Ser Asn Ile Met Leu Ala Asp Glu Arg<br>485 490 495 | 1723 |
| gtc ctg tgg ctg gcg cag agg gaa gct aaa gcc tgc agt agg att gtg<br>Val Leu Trp Leu Ala Gln Arg Glu Ala Lys Ala Cys Ser Arg Ile Val<br>500 505 510 515 | 1771 |
| cag tgt ctt cag cgc att gct acc tac cgg cta gcc ggt gga gct cac<br>Gln Cys Leu Gln Arg Ile Ala Thr Tyr Arg Leu Ala Gly Gly Ala His<br>520 525 530 | 1819 |
| gtt tat tca aca tat tca ccc aat att gct ctg gaa gct tat gtc atc<br>Val Tyr Ser Thr Tyr Ser Pro Asn Ile Ala Leu Glu Ala Tyr Val Ile<br>535 540 545 | 1867 |
| aag tct act ggc ttc acg ggg atg acc tgt acc gtg ttc cag aaa gtg<br>Lys Ser Thr Gly Phe Thr Gly Met Thr Cys Thr Val Phe Gln Lys Val<br>550 555 560 | 1915 |
| gca gcc tct gat cgt aca gga ctt tcg gat tat ggg agg cgg gat cca<br>Ala Ala Ser Asp Arg Thr Gly Leu Ser Asp Tyr Gly Arg Arg Asp Pro<br>565 570 575 | 1963 |
| gag gga aac ctg gat aag cag ctg agc ttt aag tgc aat gtt tca aat<br>Glu Gly Asn Leu Asp Lys Gln Leu Ser Phe Lys Cys Asn Val Ser Asn<br>580 585 590 595 | 2011 |
| aca ttt tcg agt ctg gca cta aag aat act att gtg gag gct tct att<br>Thr Phe Ser Ser Leu Ala Leu Lys Asn Thr Ile Val Glu Ala Ser Ile<br>600 605 610 | 2059 |
| cag ctt cct cct tcc ctt ttc tca cca aag caa aaa aga gaa ctc aga<br>Gln Leu Pro Pro Ser Leu Phe Ser Pro Lys Gln Lys Arg Glu Leu Arg<br>615 620 625 | 2107 |
| cca act gat gac tct ctt tac aag ctt caa ctc att gca ttc cgc aat<br>Pro Thr Asp Asp Ser Leu Tyr Lys Leu Gln Leu Ile Ala Phe Arg Asn<br>630 635 640 | 2155 |
| gga aag ctt ttt cca gcc act gga aat tca aca aat ttg gct gat gat<br>Gly Lys Leu Phe Pro Ala Thr Gly Asn Ser Thr Asn Leu Ala Asp Asp<br>645 650 655 | 2203 |
| gga aaa cga cgt act gtg gtt acc cct gtg att ctc acc aaa ata gat<br>Gly Lys Arg Arg Thr Val Val Thr Pro Val Ile Leu Thr Lys Ile Asp<br>660 665 670 675 | 2251 |
| ggt gtg aat gta gat acc cac cac atc cct gtt aat gtg aca ctg cgt<br>Gly Val Asn Val Asp Thr His His Ile Pro Val Asn Val Thr Leu Arg<br>680 685 690 | 2299 |
| cga att gca cat gga gca gat gct gtt gca gcc cgg tgg gat ttc gat<br>Arg Ile Ala His Gly Ala Asp Ala Val Ala Ala Arg Trp Asp Phe Asp<br>695 700 705 | 2347 |
| ttg ctg aac gga caa gga ggc tgg aag tca gat ggg tgc cat ata ctc<br>Leu Leu Asn Gly Gln Gly Gly Trp Lys Ser Asp Gly Cys His Ile Leu<br>710 715 720 | 2395 |
| tat tca gat gaa aat atc act acg att cag tgc tac tcc ctt agt aac<br>Tyr Ser Asp Glu Asn Ile Thr Thr Ile Gln Cys Tyr Ser Leu Ser Asn<br>725 730 735 | 2443 |
| tat gca gtt tta atg gat ttg acg gga tct gaa cta tac acc cag gcg<br>Tyr Ala Val Leu Met Asp Leu Thr Gly Ser Glu Leu Tyr Thr Gln Ala<br>740 745 750 755 | 2491 |
| gcc agc ctc ctg cat cct gtg gtt tat act acc gct atc att ctc ctc<br>Ala Ser Leu Leu His Pro Val Val Tyr Thr Thr Ala Ile Ile Leu Leu<br>760 765 770 | 2539 |
| tta tgt ctc tta gcc gtc att gtc agt tac ata tac cat cac agt ttg<br>Leu Cys Leu Leu Ala Val Ile Val Ser Tyr Ile Tyr His His Ser Leu<br>775 780 785 | 2587 |

```
att aga atc agc ctc aag agc tgg cac atg ctt gtg aac ttg tgc ttt    2635
Ile Arg Ile Ser Leu Lys Ser Trp His Met Leu Val Asn Leu Cys Phe
        790             795                 800 cat att ttc cta acc tgt gtg gtc ttt gtg gga gga ata acc cag act    2683
His Ile Phe Leu Thr Cys Val Val Phe Val Gly Gly Ile Thr Gln Thr
        805             810                 815 agg aat gcc agc atc tgc caa gca gtt ggg ata att ctt cac tat tcc    2731
Arg Asn Ala Ser Ile Cys Gln Ala Val Gly Ile Ile Leu His Tyr Ser
820             825                 830                 835 acc ctt gcc aca gta cta tgg gta gga gtg aca gct cga aat atc tac    2779
Thr Leu Ala Thr Val Leu Trp Val Gly Val Thr Ala Arg Asn Ile Tyr
                840                 845                 850 aaa caa gtc act aaa aaa gct aaa aga tgc cag gat cct gat gaa cca    2827
Lys Gln Val Thr Lys Lys Ala Lys Arg Cys Gln Asp Pro Asp Glu Pro
            855                 860                 865 cca cct cca cca aga cca atg ctc aga ttt tac ctg att ggt ggt ggt    2875
Pro Pro Pro Pro Arg Pro Met Leu Arg Phe Tyr Leu Ile Gly Gly Gly
        870                 875                 880 atc ccc atc att gtt tgc ggc ata act gca gca gcg aac att aag aat    2923
Ile Pro Ile Ile Val Cys Gly Ile Thr Ala Ala Ala Asn Ile Lys Asn
885                 890                 895 tac ggc agt cgg cca aac gca ccc tat tgc tgg atg gca tgg gaa ccc    2971
Tyr Gly Ser Arg Pro Asn Ala Pro Tyr Cys Trp Met Ala Trp Glu Pro
900             905                 910                 915 tcc ttg gga gcc ttc tat ggg cca gcc agc ttc atc act ttt gta aac    3019
Ser Leu Gly Ala Phe Tyr Gly Pro Ala Ser Phe Ile Thr Phe Val Asn
                920                 925                 930 tgc atg tac ttt ctg agc ata ttt att cag ttg aaa aga cac cct gag    3067
Cys Met Tyr Phe Leu Ser Ile Phe Ile Gln Leu Lys Arg His Pro Glu
            935                 940                 945 cgc aaa tat gag ctt aag gag ccc acg gag gag caa cag aga ttg gca    3115
Arg Lys Tyr Glu Leu Lys Glu Pro Thr Glu Glu Gln Gln Arg Leu Ala
        950                 955                 960 gcc aat gaa aat ggc gaa ata aat cat cag gat tca atg tct ttg tct    3163
Ala Asn Glu Asn Gly Glu Ile Asn His Gln Asp Ser Met Ser Leu Ser
965                 970                 975 ctg att tct aca tca gcc ttg gaa aat gag cac act ttt cat tct cag    3211
Leu Ile Ser Thr Ser Ala Leu Glu Asn Glu His Thr Phe His Ser Gln
980                 985                 990                 995 ctc ttg ggg gcc agc ctt act ttg ctc tta tat gtt gca ctg tgg atg    3259
Leu Leu Gly Ala Ser Leu Thr Leu Leu Leu Tyr Val Ala Leu Trp Met
                1000                1005                1010 ttt ggg gct ttg gct gtt tct ttg tat tac cct ttg gac ttg gtt ttt    3307
Phe Gly Ala Leu Ala Val Ser Leu Tyr Tyr Pro Leu Asp Leu Val Phe
            1015                1020                1025 agc ttc gtt ttt gga gcc aca agt tta agc ttc agt gcg ttc ttc gtg    3355
Ser Phe Val Phe Gly Ala Thr Ser Leu Ser Phe Ser Ala Phe Phe Val
        1030                1035                1040 gtc cac cat tgt gtt aat agg gag gat gtt aga ctt gcg tgg atc atg    3403
Val His His Cys Val Asn Arg Glu Asp Val Arg Leu Ala Trp Ile Met
    1045                1050                1055 act tgc tgc cca gga cgg agc tcg tat tca gtg caa gtc aac gtc cag    3451
Thr Cys Cys Pro Gly Arg Ser Ser Tyr Ser Val Gln Val Asn Val Gln
1060                1065                1070                1075 ccc ccc aac tct aat ggg acg aat gga gag gca ccc aaa tgc ccc aat    3499
Pro Pro Asn Ser Asn Gly Thr Asn Gly Glu Ala Pro Lys Cys Pro Asn
                1080                1085                1090 agc agt gcg gag tct tca tgc aca aac aaa agt gct tca agc ttc aaa    3547
Ser Ser Ala Glu Ser Ser Cys Thr Asn Lys Ser Ala Ser Ser Phe Lys
            1095                1100                1105
```

| | | |
|---|---|---|
| aat tcc tcc cag ggc tgc aaa tta aca aac ttg cag gcg gct gca gct<br>Asn Ser Ser Gln Gly Cys Lys Leu Thr Asn Leu Gln Ala Ala Ala Ala<br>          1110                  1115                  1120 | | 3595 |
| cag tgc cat gcc aat tct tta cct ttg aac tcc acc cct cag ctt gat<br>Gln Cys His Ala Asn Ser Leu Pro Leu Asn Ser Thr Pro Gln Leu Asp<br>1125                  1130                  1135 | | 3643 |
| aat agt ctg aca gaa cat tca atg gac aat gat att aaa atg cac gtg<br>Asn Ser Leu Thr Glu His Ser Met Asp Asn Asp Ile Lys Met His Val<br>1140                  1145                  1150                  1155 | | 3691 |
| gcg cct tta gaa gtt cag ttt cga aca aat gtg cac tca agc cgc cac<br>Ala Pro Leu Glu Val Gln Phe Arg Thr Asn Val His Ser Ser Arg His<br>          1160                  1165                  1170 | | 3739 |
| cat aaa aac aga agt aaa gga cac cgg gca agc cga ctc aca gtc ctg<br>His Lys Asn Arg Ser Lys Gly His Arg Ala Ser Arg Leu Thr Val Leu<br>1175                  1180                  1185 | | 3787 |
| aga gaa tat gcc tac gat gtc cca acg agc gtg gaa gga agc gtg cag<br>Arg Glu Tyr Ala Tyr Asp Val Pro Thr Ser Val Glu Gly Ser Val Gln<br>          1190                  1195                  1200 | | 3835 |
| aac ggc tta cct aaa agc cgg ctg ggc aat aac gaa gga cac tcg agg<br>Asn Gly Leu Pro Lys Ser Arg Leu Gly Asn Asn Glu Gly His Ser Arg<br>          1205                  1210                  1215 | | 3883 |
| agc cga aga gct tat tta gcc tac aga gag aga cag tac aac cca ccc<br>Ser Arg Arg Ala Tyr Leu Ala Tyr Arg Glu Arg Gln Tyr Asn Pro Pro<br>1220                  1225                  1230                  1235 | | 3931 |
| cag caa gac agc agc gat gct tgt agc aca ctt ccc aaa agt agc aga<br>Gln Gln Asp Ser Ser Asp Ala Cys Ser Thr Leu Pro Lys Ser Ser Arg<br>          1240                  1245                  1250 | | 3979 |
| aat ttt gaa aag cca gtt tca acc act agt aaa aaa gat gcg tta agg<br>Asn Phe Glu Lys Pro Val Ser Thr Thr Ser Lys Lys Asp Ala Leu Arg<br>          1255                  1260                  1265 | | 4027 |
| aag cca gct gtg gtt gaa ctt gaa aat cag caa aaa tct tat ggc ctc<br>Lys Pro Ala Val Val Glu Leu Glu Asn Gln Gln Lys Ser Tyr Gly Leu<br>1270                  1275                  1280 | | 4075 |
| aac ttg gcc att cag aat gga cca att aaa agc aat ggg cag gag gga<br>Asn Leu Ala Ile Gln Asn Gly Pro Ile Lys Ser Asn Gly Gln Glu Gly<br>          1285                  1290                  1295 | | 4123 |
| ccc ttg ctc ggt acc gat agc act ggc aat gtt agg act gga tta tgg<br>Pro Leu Leu Gly Thr Asp Ser Thr Gly Asn Val Arg Thr Gly Leu Trp<br>1300                  1305                  1310                  1315 | | 4171 |
| aaa cac gaa act act gtg taacattgct gggcttccta ggcagaaatt<br>Lys His Glu Thr Thr Val<br>          1320 | | 4219 |
| catataaact gtgatactca cattccttga agctatgagc atttaaaaac tgtttacagc | | 4279 |
| caccataggg attcaaaaga atttggaata aactttgaag ttttggattt tacttatttt | | 4339 |
| tatcccccaaa ttgttgctat tttttaggat ctgaaacaaa atctttctaa aacattgttt | | 4399 |
| tagttgtcaa agcaccaaca ggacattttg ggatgtgaaa tgtaatttct tggaatctgt | | 4459 |
| aatttgtact tagtatttca ggcttgtatt taatataata aataggtgtt tgttattgtg | | 4519 |
| tcaaaaaaaa aaaaaaa | | 4536 |

<210> SEQ ID NO 2
<211> LENGTH: 1321
<212> TYPE: PRT
<213> ORGANISM: Homo sapiens

<400> SEQUENCE: 2

```
Met Glu Pro Pro Gly Arg Arg Gly Arg Ala Gln Pro Pro Leu Leu
 1               5                  10                  15

Leu Pro Leu Ser Leu Leu Ala Leu Ala Leu Gly Gly Gly Gly Gly
            20                  25                  30

Gly Gly Ala Ala Ala Leu Pro Ala Gly Cys Lys His Asp Gly Arg
         35                  40                  45

Pro Arg Gly Ala Gly Arg Ala Gly Ala Ala Glu Gly Lys Val Val
 50                  55                  60

Cys Ser Ser Leu Glu Leu Ala Gln Val Leu Pro Pro Asp Thr Leu Pro
 65                  70                  75                  80

Asn Arg Thr Val Thr Leu Ile Leu Ser Asn Asn Lys Ile Ser Glu Leu
                 85                  90                  95

Lys Asn Gly Ser Phe Ser Gly Leu Ser Leu Leu Glu Arg Leu Asp Leu
                100                 105                 110

Arg Asn Asn Leu Ile Ser Ser Ile Asp Pro Gly Ala Phe Trp Gly Leu
                115                 120                 125

Ser Ser Leu Lys Arg Leu Asp Leu Thr Asn Asn Arg Ile Gly Cys Leu
130                 135                 140

Asn Ala Asp Ile Phe Arg Gly Leu Thr Asn Leu Val Arg Leu Asn Leu
145                 150                 155                 160

Ser Gly Asn Leu Phe Ser Ser Leu Ser Gln Gly Thr Phe Asp Tyr Leu
                165                 170                 175

Ala Ser Leu Arg Ser Leu Glu Phe Gln Thr Glu Tyr Leu Leu Cys Asp
                180                 185                 190

Cys Asn Ile Leu Trp Met His Arg Trp Val Lys Glu Lys Asn Ile Thr
                195                 200                 205

Val Arg Asp Thr Arg Cys Val Tyr Pro Lys Ser Leu Gln Ala Gln Pro
210                 215                 220

Val Thr Gly Val Lys Gln Glu Leu Leu Thr Cys Asp Pro Pro Leu Glu
225                 230                 235                 240

Leu Pro Ser Phe Tyr Met Thr Pro Ser His Arg Gln Val Val Phe Glu
                245                 250                 255

Gly Asp Ser Leu Pro Phe Gln Cys Met Ala Ser Tyr Ile Asp Gln Asp
                260                 265                 270

Met Gln Val Leu Trp Tyr Gln Asp Gly Arg Ile Val Glu Thr Asp Glu
                275                 280                 285

Ser Gln Gly Ile Phe Val Glu Lys Asn Met Ile His Asn Cys Ser Leu
                290                 295                 300

Ile Ala Ser Ala Leu Thr Ile Ser Asn Ile Gln Ala Gly Ser Thr Gly
305                 310                 315                 320

Asn Trp Gly Cys His Val Gln Thr Lys Arg Gly Asn Asn Thr Arg Thr
                325                 330                 335

Val Asp Ile Val Val Leu Glu Ser Ser Ala Gln Tyr Cys Pro Pro Glu
                340                 345                 350

Arg Val Val Asn Asn Lys Gly Asp Phe Arg Trp Pro Arg Thr Leu Ala
                355                 360                 365

Gly Ile Thr Ala Tyr Leu Gln Cys Thr Arg Asn Thr His Gly Ser Gly
                370                 375                 380

Ile Tyr Pro Gly Asn Pro Gln Asp Glu Arg Lys Ala Trp Arg Arg Cys
385                 390                 395                 400

Asp Arg Gly Gly Phe Trp Ala Asp Asp Tyr Ser Arg Cys Gln Tyr
                405                 410                 415
```

```
Ala Asn Asp Val Thr Arg Val Leu Tyr Met Phe Asn Gln Met Pro Leu
            420                 425                 430

Asn Leu Thr Asn Ala Val Ala Thr Ala Arg Gln Leu Leu Ala Tyr Thr
        435                 440                 445

Val Glu Ala Ala Asn Phe Ser Asp Lys Met Asp Val Ile Phe Val Ala
450                 455                 460

Glu Met Ile Glu Lys Phe Gly Arg Phe Thr Lys Glu Lys Ser Lys
465             470              475              480

Glu Leu Gly Asp Val Met Val Asp Ile Ala Ser Asn Ile Met Leu Ala
                485                 490                 495

Asp Glu Arg Val Leu Trp Leu Ala Gln Arg Glu Ala Lys Ala Cys Ser
            500                 505                 510

Arg Ile Val Gln Cys Leu Gln Arg Ile Ala Thr Tyr Arg Leu Ala Gly
        515                 520                 525

Gly Ala His Val Tyr Ser Thr Tyr Ser Pro Asn Ile Ala Leu Glu Ala
        530                 535                 540

Tyr Val Ile Lys Ser Thr Gly Phe Thr Gly Met Thr Cys Thr Val Phe
545                 550                 555                 560

Gln Lys Val Ala Ala Ser Asp Arg Thr Gly Leu Ser Asp Tyr Gly Arg
                565                 570                 575

Arg Asp Pro Glu Gly Asn Leu Asp Lys Gln Leu Ser Phe Lys Cys Asn
            580                 585                 590

Val Ser Asn Thr Phe Ser Ser Leu Ala Leu Lys Asn Thr Ile Val Glu
        595                 600                 605

Ala Ser Ile Gln Leu Pro Pro Ser Leu Phe Ser Pro Lys Gln Lys Arg
        610                 615                 620

Glu Leu Arg Pro Thr Asp Asp Ser Leu Tyr Lys Leu Gln Leu Ile Ala
625                 630                 635                 640

Phe Arg Asn Gly Lys Leu Phe Pro Ala Thr Gly Asn Ser Thr Asn Leu
                645                 650                 655

Ala Asp Asp Gly Lys Arg Arg Thr Val Val Thr Pro Val Ile Leu Thr
            660                 665                 670

Lys Ile Asp Gly Val Asn Val Asp Thr His His Ile Pro Val Asn Val
        675                 680                 685

Thr Leu Arg Arg Ile Ala His Gly Ala Asp Ala Val Ala Ala Arg Trp
690                 695                 700

Asp Phe Asp Leu Leu Asn Gly Gln Gly Gly Trp Lys Ser Asp Gly Cys
705                 710                 715                 720

His Ile Leu Tyr Ser Asp Glu Asn Ile Thr Thr Ile Gln Cys Tyr Ser
                725                 730                 735

Leu Ser Asn Tyr Ala Val Leu Met Asp Leu Thr Gly Ser Glu Leu Tyr
            740                 745                 750

Thr Gln Ala Ala Ser Leu Leu His Pro Val Val Tyr Thr Thr Ala Ile
        755                 760                 765

Ile Leu Leu Leu Cys Leu Leu Ala Val Ile Val Ser Tyr Ile Tyr His
        770                 775                 780

His Ser Leu Ile Arg Ile Ser Leu Lys Ser Trp His Met Leu Val Asn
785                 790                 795                 800

Leu Cys Phe His Ile Phe Leu Thr Cys Val Val Phe Val Gly Gly Ile
                805                 810                 815

Thr Gln Thr Arg Asn Ala Ser Ile Cys Gln Ala Val Gly Ile Ile Leu
            820                 825                 830

His Tyr Ser Thr Leu Ala Thr Val Leu Trp Val Gly Val Thr Ala Arg
        835                 840                 845
```

-continued

```
Asn Ile Tyr Lys Gln Val Thr Lys Lys Ala Lys Arg Cys Gln Asp Pro
        850                 855                 860

Asp Glu Pro Pro Pro Pro Arg Pro Met Leu Arg Phe Tyr Leu Ile
865                 870                 875                 880

Gly Gly Gly Ile Pro Ile Ile Val Cys Gly Ile Thr Ala Ala Ala Asn
                    885                 890                 895

Ile Lys Asn Tyr Gly Ser Arg Pro Asn Ala Pro Tyr Cys Trp Met Ala
            900                 905                 910

Trp Glu Pro Ser Leu Gly Ala Phe Tyr Gly Pro Ala Ser Phe Ile Thr
        915                 920                 925

Phe Val Asn Cys Met Tyr Phe Leu Ser Ile Phe Ile Gln Leu Lys Arg
        930                 935                 940

His Pro Glu Arg Lys Tyr Glu Leu Lys Glu Pro Thr Glu Gln Gln
945                 950                 955                 960

Arg Leu Ala Ala Asn Glu Asn Gly Glu Ile Asn His Gln Asp Ser Met
                965                 970                 975

Ser Leu Ser Leu Ile Ser Thr Ser Ala Leu Glu Asn Glu His Thr Phe
            980                 985                 990

His Ser Gln Leu Leu Gly Ala Ser Leu Thr Leu Leu Leu Tyr Val Ala
        995                 1000                1005

Leu Trp Met Phe Gly Ala Leu Ala Val Ser Leu Tyr Tyr Pro Leu Asp
    1010                1015                1020

Leu Val Phe Ser Phe Val Phe Gly Ala Thr Ser Leu Ser Phe Ser Ala
1025                1030                1035                1040

Phe Phe Val Val His His Cys Val Asn Arg Glu Asp Val Arg Leu Ala
                1045                1050                1055

Trp Ile Met Thr Cys Cys Pro Gly Arg Ser Ser Tyr Ser Val Gln Val
            1060                1065                1070

Asn Val Gln Pro Pro Asn Ser Asn Gly Thr Asn Gly Glu Ala Pro Lys
        1075                1080                1085

Cys Pro Asn Ser Ser Ala Glu Ser Ser Cys Thr Asn Lys Ser Ala Ser
    1090                1095                1100

Ser Phe Lys Asn Ser Ser Gln Gly Cys Lys Leu Thr Asn Leu Gln Ala
1105                1110                1115                1120

Ala Ala Ala Gln Cys His Ala Asn Ser Leu Pro Leu Asn Ser Thr Pro
                1125                1130                1135

Gln Leu Asp Asn Ser Leu Thr Glu His Ser Met Asp Asn Asp Ile Lys
            1140                1145                1150

Met His Val Ala Pro Leu Glu Val Gln Phe Arg Thr Asn Val His Ser
        1155                1160                1165

Ser Arg His His Lys Asn Arg Ser Lys Gly His Arg Ala Ser Arg Leu
    1170                1175                1180

Thr Val Leu Arg Glu Tyr Ala Tyr Asp Val Pro Thr Ser Val Glu Gly
1185                1190                1195                1200

Ser Val Gln Asn Gly Leu Pro Lys Ser Arg Leu Gly Asn Asn Glu Gly
                1205                1210                1215

His Ser Arg Ser Arg Ala Tyr Leu Ala Tyr Arg Glu Arg Gln Tyr
            1220                1225                1230

Asn Pro Pro Gln Gln Asp Ser Ser Asp Ala Cys Ser Thr Leu Pro Lys
        1235                1240                1245

Ser Ser Arg Asn Phe Glu Lys Pro Val Ser Thr Thr Ser Lys Lys Asp
    1250                1255                1260

Ala Leu Arg Lys Pro Ala Val Val Glu Leu Glu Asn Gln Gln Lys Ser
1265                1270                1275                1280
```

```
                              Tyr Gly Leu Asn Leu Ala Ile Gln Asn Gly Pro Ile Lys Ser Asn Gly
                                  1285                1290                1295

Gln Glu Gly Pro Leu Leu Gly Thr Asp Ser Thr Gly Asn Val Arg Thr
                                  1300                1305                1310

Gly Leu Trp Lys His Glu Thr Thr Val
                                  1315                1320

<210> SEQ ID NO 3
<211> LENGTH: 4303
<212> TYPE: DNA
<213> ORGANISM: Homo sapiens
<220> FEATURE:
<221> NAME/KEY: CDS
<222> LOCATION: (83)..(1759)

<400> SEQUENCE: 3
ccgcgctcct gcccgcccgg gctccggggc ggcccgctag gccagtgcgc cgccgctcgc        60
cccgcaggcc ccggcccgca gc atg gag cca ccc gga cgc cgg cgg ggc cgc       112
                          Met Glu Pro Pro Gly Arg Arg Arg Gly Arg
                            1               5                  10 gcg cag ccg ccg ctg ttg ctg ccg ctc tcg ctg tta gcg ctg ctc gcg       160
Ala Gln Pro Pro Leu Leu Leu Pro Leu Ser Leu Leu Ala Leu Leu Ala
             15                  20                  25 ctg ctg gga ggc ggc ggc ggc ggc gcc gcg gcg ctg ccc gcc ggc            208
Leu Leu Gly Gly Gly Gly Gly Gly Ala Ala Ala Leu Pro Ala Gly
         30                  35                  40 tgc aag cac gat ggg cgg ccc cga ggg gct ggc agg gcg gcg ggc gcc       256
Cys Lys His Asp Gly Arg Pro Arg Gly Ala Gly Arg Ala Ala Gly Ala
     45                  50                  55 gcc gag ggc aag gtg gtg tgc agc agc ctg gaa ctc gcg cag gtc ctg       304
Ala Glu Gly Lys Val Val Cys Ser Ser Leu Glu Leu Ala Gln Val Leu
 60                  65                  70 ccc cca gat act ctg ccc aac cgc acg gtc acc ctg att ctg agt aac       352
Pro Pro Asp Thr Leu Pro Asn Arg Thr Val Thr Leu Ile Leu Ser Asn
 75                  80                  85                  90 aat aag ata tcc gag ctg aag aat ggc tca ttt tct ggg tta agt ctc       400
Asn Lys Ile Ser Glu Leu Lys Asn Gly Ser Phe Ser Gly Leu Ser Leu
             95                 100                 105 ctt gaa aga ttg gac ctc cga aac aat ctt att agt agt ata gat cca       448
Leu Glu Arg Leu Asp Leu Arg Asn Asn Leu Ile Ser Ser Ile Asp Pro
         110                 115                 120 ggt gcc ttc tgg gga ctg tca tct cta aaa aga ttg gat ctg aca aac       496
Gly Ala Phe Trp Gly Leu Ser Ser Leu Lys Arg Leu Asp Leu Thr Asn
     125                 130                 135 aat cga ata gga tgt ctg aat gca gac ata ttt cga gga ctc acc aat       544
Asn Arg Ile Gly Cys Leu Asn Ala Asp Ile Phe Arg Gly Leu Thr Asn
 140                 145                 150 ctg gtt cgg cta aac ctt tcg ggg aat ttg ttt tct tca tta tct caa       592
Leu Val Arg Leu Asn Leu Ser Gly Asn Leu Phe Ser Ser Leu Ser Gln
155                 160                 165                 170 gga act ttt gat tat ctt gcg tca tta cgg tct ttg gaa ttc cag act       640
Gly Thr Phe Asp Tyr Leu Ala Ser Leu Arg Ser Leu Glu Phe Gln Thr
             175                 180                 185 gag tat ctt ttg tgt gac tgt aac ata ctg tgg atg cat cgc tgg gta       688
Glu Tyr Leu Leu Cys Asp Cys Asn Ile Leu Trp Met His Arg Trp Val
         190                 195                 200 aag gag aag aac atc acg gta cgg gat acc agg tgt gtt tat cct aag       736
Lys Glu Lys Asn Ile Thr Val Arg Asp Thr Arg Cys Val Tyr Pro Lys
     205                 210                 215
```

```
tca ctg cag gcc caa cca gtc aca ggc gtg aag cag gag ctg ttg aca      784
Ser Leu Gln Ala Gln Pro Val Thr Gly Val Lys Gln Glu Leu Leu Thr
    220                 225                 230 tgc gac cct ccg ctt gaa ttg ccg tct ttc tac atg act cca tct cat      832
Cys Asp Pro Pro Leu Glu Leu Pro Ser Phe Tyr Met Thr Pro Ser His
235                 240                 245                 250 cgc caa gtt gtg ttt gaa gga gac agc ctt cct ttc cag tgc atg gct      880
Arg Gln Val Val Phe Glu Gly Asp Ser Leu Pro Phe Gln Cys Met Ala
                255                 260                 265 tca tat att gat cag gac atg caa gtg ttg tgg tat cag gat ggg aga      928
Ser Tyr Ile Asp Gln Asp Met Gln Val Leu Trp Tyr Gln Asp Gly Arg
            270                 275                 280 ata gtt gaa acc gat gaa tcg caa ggt att ttt gtt gaa aag aac atg      976
Ile Val Glu Thr Asp Glu Ser Gln Gly Ile Phe Val Glu Lys Asn Met
        285                 290                 295 att cac aac tgc tcc ttg att gca agt gcc cta acc att tct aat att     1024
Ile His Asn Cys Ser Leu Ile Ala Ser Ala Leu Thr Ile Ser Asn Ile
300                 305                 310 cag gct gga tct act gga aat tgg ggc tgt cat gtc cag acc aaa cgt     1072
Gln Ala Gly Ser Thr Gly Asn Trp Gly Cys His Val Gln Thr Lys Arg
315                 320                 325                 330 ggg aat aat acg agg act gtg gat att gtg gta tta gag agt tct gca     1120
Gly Asn Asn Thr Arg Thr Val Asp Ile Val Val Leu Glu Ser Ser Ala
                335                 340                 345 cag tac tgt ccg cca gag agg gtg gta aac aac aaa ggt gac ttc aga     1168
Gln Tyr Cys Pro Pro Glu Arg Val Val Asn Asn Lys Gly Asp Phe Arg
            350                 355                 360 tgg ccc aga aca ttg gca ggc att act gca tat ctg cag tgt acg cgg     1216
Trp Pro Arg Thr Leu Ala Gly Ile Thr Ala Tyr Leu Gln Cys Thr Arg
        365                 370                 375 aac acc cat ggc agt ggg ata tat ccc gga aac cca cag gat gag aga     1264
Asn Thr His Gly Ser Gly Ile Tyr Pro Gly Asn Pro Gln Asp Glu Arg
380                 385                 390 aaa gct tgg cgc aga tgt gat aga ggt ggc ttt tgg gca gat gat gat     1312
Lys Ala Trp Arg Arg Cys Asp Arg Gly Gly Phe Trp Ala Asp Asp Asp
395                 400                 405                 410 tat tct cgc tgt cag tat gca aat gat gtc act aga gtt ctt tat atg     1360
Tyr Ser Arg Cys Gln Tyr Ala Asn Asp Val Thr Arg Val Leu Tyr Met
                415                 420                 425 ttt aat cag atg ccc ctc aat ctt acc aat gcc gtg gca aca gct cga     1408
Phe Asn Gln Met Pro Leu Asn Leu Thr Asn Ala Val Ala Thr Ala Arg
            430                 435                 440 cag tta ctg gct tac act gtg gaa gca gcc aac ttt tct gac aaa atg     1456
Gln Leu Leu Ala Tyr Thr Val Glu Ala Ala Asn Phe Ser Asp Lys Met
        445                 450                 455 gat gtt ata ttt gtg gca gaa atg att gaa aaa ttt gga aga ttt acc     1504
Asp Val Ile Phe Val Ala Glu Met Ile Glu Lys Phe Gly Arg Phe Thr
460                 465                 470 aag gag gaa aaa tca aaa gag cta ggt gac gtg atg gtt gac att gca     1552
Lys Glu Glu Lys Ser Lys Glu Leu Gly Asp Val Met Val Asp Ile Ala
475                 480                 485                 490 agt aac atc atg ttg gct gat gaa cgt gtc ctg tgg ctg gcg cag agg     1600
Ser Asn Ile Met Leu Ala Asp Glu Arg Val Leu Trp Leu Ala Gln Arg
                495                 500                 505 gaa gct aaa gcc tgc agt agg atc gtg cag tgt ctt cag cgc att gct     1648
Glu Ala Lys Ala Cys Ser Arg Ile Val Gln Cys Leu Gln Arg Ile Ala
            510                 515                 520 acc tac cgg cta gcc ggt gga gct cac gtt tat tca aca att gac ttt     1696
Thr Tyr Arg Leu Ala Gly Gly Ala His Val Tyr Ser Thr Ile Asp Phe
        525                 530                 535
```

| | |
|---|---|
| tca agt att cac cca ata ttg ctc tgg aag ctt atg tca tca agt cta<br>Ser Ser Ile His Pro Ile Leu Leu Trp Lys Leu Met Ser Ser Ser Leu<br>540 545 550 | 1744 |
| ctg gct tca cgg gga tgacctgtac cgtgttccag aaagtggcag cctctgatcg<br>Leu Ala Ser Arg Gly<br>555 | 1799 |
| tacaggactt tcggattatg ggaggcggga tccagaggga aacctggata agcagctgag | 1859 |
| ctttaagtgc aatgtttcaa atacattttc gagtctggca ctaaagaata ctattgtgga | 1919 |
| ggcttctatt cagcttcctc cttcccttttt ctcaccaaag caaaaaagag aactcagacc | 1979 |
| aactgatgac tctctttaca agcttcaact cattgcattc cgcaatggaa agctttttcc | 2039 |
| agccactgga aattcaacaa atttggctga tgatggaaaa cgacgtactg tggttacccc | 2099 |
| tgtgattctc accaaaatag atggtgtgaa tgtagatacc caccacatcc ctgttaatgt | 2159 |
| gacactgcgt cgaattgcac atggagcaga tgctgttgca gcccggtggg atttcgattt | 2219 |
| gctgaacgga caaggaggct ggaagtcaga tgggtgccat atactctatt cagatgaaaa | 2279 |
| tatcactacg attcagtgct actcccttag taactatgca gttttaatgg atttgacggg | 2339 |
| atctgaacta tacacccagg cggccagcct cctgcatcct gtggtttata ctaccgctat | 2399 |
| cattctcctc ttatgtctct tagccgtcat tgtcagttac atataccatc acagtttgat | 2459 |
| tagaatcagc ctcaagagct ggcacatgct tgtgaacttg tgctttcata ttttcctaac | 2519 |
| ctgtgtggtc tttgtgggag gaataaccca gactaggaat gccagcatct gccaagcagt | 2579 |
| tgggataatt cttcactatt ccacccttgc cacagtacta tgggtaggag tgacagctcg | 2639 |
| aaatatctac aaacaagtca ctaaaaaagc taaaagatgc caggatcctg atgaaccacc | 2699 |
| acctccacca agaccaatgc tcagattta cctgattggt ggtggtatcc ccatcattgt | 2759 |
| ttgcggcata actgcagcag cgaacattaa gaattacggc agtcggccaa acgcacccta | 2819 |
| ttgctggatg gcatgggaac cctccttggg agccttctat gggccagcca gcttcatcac | 2879 |
| ttttgtaaac tgcatgtact ttctgagcat atttattcag ttgaaaagac accctgagcg | 2939 |
| caaatatgag cttaaggagc ccacggagga gcaacagaga ttggcagcca atgaaaatgg | 2999 |
| cgaaataaat catcaggatt caatgtcttt gtctctgatt tctacatcag ccttggaaaa | 3059 |
| tgagcacact tttcattctc agctcttggg ggccagcctt actttgctct tatatgttgc | 3119 |
| actgtgatg tttggggctt tggctgtttc tttgtattac cctttggact tggttttttag | 3179 |
| cttcgttttt ggagccacaa gtttaagctt cagtgcgttc ttcatggtcc accattgtgt | 3239 |
| taatagggag gatgttagac ttgcgtggat catgacttgc tgcccaggac ggagctcgta | 3299 |
| ttcagtgcaa gtcaacgtcc agcccccccaa ctctaatggg acgaatggag aggcacccaa | 3359 |
| atgccccaat agcagtgcgg agtcttcatg cacaaacaaa agtgcttcaa gcttcaaaaa | 3419 |
| ttcctcccag ggctgcaaat aacaaactt gcaggcggct gcagctcagt gccatgccaa | 3479 |
| ttctttacct ttgaactcca cccctcagct tgataatagt ctgacagaac attcaatgga | 3539 |
| caatgatatt aaaatgcacg tggcgccttt agaagttcag tttcgaacaa atgtgcactc | 3599 |
| aagccgccac cataaaaaca gaagtaaagg acaccgggca agccgactca cagtcctgag | 3659 |
| agaatatgcc tacgatgtcc caacgagcgt ggaaggaagc gtgcagaacg gcttacctaa | 3719 |
| aagccggctg ggcaataacg aaggacactc gaggagccga agagcttatt tagcctacag | 3779 |
| agagagacag tacaacccac cccagcaaga cagcagcgat gcttgtagca cacttcccaa | 3839 |
| aagtagcaga aattttgaaa agccagtttc aaccactagt aaaaaagatg cgttaaggaa | 3899 |
| gccagctgtg gttgaacttg aaaatcagca aaatcttat ggcctcaact tggccattca | 3959 |

-continued

```
gaatggacca attaaaagca atgggcagga gggacccttg ctcggtaccg atagcactgg      4019
caatgttagg actggattat ggaaacacga aactactgtg taacattgct gggcttccta      4079
ggcagaaatt catataaact gtgatactca cattccttga agctatgagc atttaaaaac      4139
tgtttacagc caccataggg attcaaaaga atttggaata aactttgaag ttttggattt      4199
tacttatttt tatccccaaa ttgttgctat ttttaggat ctgaaacaaa atctttctaa       4259
aacattgttt tagttgtcaa agcaccaaca ggacattttg ggat                      4303
```

<210> SEQ ID NO 4
<211> LENGTH: 559
<212> TYPE: PRT
<213> ORGANISM: Homo sapiens

<400> SEQUENCE: 4

```
Met Glu Pro Pro Gly Arg Arg Gly Arg Ala Gln Pro Pro Leu Leu
 1               5                  10                  15

Leu Pro Leu Ser Leu Leu Ala Leu Leu Ala Leu Leu Gly Gly Gly
                20                  25                  30

Gly Gly Gly Ala Ala Ala Leu Pro Ala Gly Cys Lys His Asp Gly Arg
        35                  40                  45

Pro Arg Gly Ala Gly Arg Ala Ala Gly Ala Ala Glu Gly Lys Val Val
    50                  55                  60

Cys Ser Ser Leu Glu Leu Ala Gln Val Leu Pro Pro Asp Thr Leu Pro
65                  70                  75                  80

Asn Arg Thr Val Thr Leu Ile Leu Ser Asn Asn Lys Ile Ser Glu Leu
                85                  90                  95

Lys Asn Gly Ser Phe Ser Gly Leu Ser Leu Leu Glu Arg Leu Asp Leu
                100                 105                 110

Arg Asn Asn Leu Ile Ser Ser Ile Asp Pro Gly Ala Phe Trp Gly Leu
            115                 120                 125

Ser Ser Leu Lys Arg Leu Asp Leu Thr Asn Asn Arg Ile Gly Cys Leu
        130                 135                 140

Asn Ala Asp Ile Phe Arg Gly Leu Thr Asn Leu Val Arg Leu Asn Leu
145                 150                 155                 160

Ser Gly Asn Leu Phe Ser Ser Leu Ser Gln Gly Thr Phe Asp Tyr Leu
                165                 170                 175

Ala Ser Leu Arg Ser Leu Glu Phe Gln Thr Glu Tyr Leu Leu Cys Asp
            180                 185                 190

Cys Asn Ile Leu Trp Met His Arg Trp Val Lys Glu Lys Asn Ile Thr
        195                 200                 205

Val Arg Asp Thr Arg Cys Val Tyr Pro Lys Ser Leu Gln Ala Gln Pro
    210                 215                 220

Val Thr Gly Val Lys Gln Glu Leu Leu Thr Cys Asp Pro Pro Leu Glu
225                 230                 235                 240

Leu Pro Ser Phe Tyr Met Thr Pro Ser His Arg Gln Val Val Phe Glu
                245                 250                 255

Gly Asp Ser Leu Pro Phe Gln Cys Met Ala Ser Tyr Ile Asp Gln Asp
            260                 265                 270

Met Gln Val Leu Trp Tyr Gln Asp Gly Arg Ile Val Glu Thr Asp Glu
        275                 280                 285

Ser Gln Gly Ile Phe Val Glu Lys Asn Met Ile His Asn Cys Ser Leu
    290                 295                 300

Ile Ala Ser Ala Leu Thr Ile Ser Asn Ile Gln Ala Gly Ser Thr Gly
305                 310                 315                 320
```

```
Asn Trp Gly Cys His Val Gln Thr Lys Arg Gly Asn Asn Thr Arg Thr
                325                 330                 335

Val Asp Ile Val Val Leu Glu Ser Ser Ala Gln Tyr Cys Pro Pro Glu
            340                 345                 350

Arg Val Val Asn Asn Lys Gly Asp Phe Arg Trp Pro Arg Thr Leu Ala
        355                 360                 365

Gly Ile Thr Ala Tyr Leu Gln Cys Thr Arg Asn Thr His Gly Ser Gly
    370                 375                 380

Ile Tyr Pro Gly Asn Pro Gln Asp Glu Arg Lys Ala Trp Arg Arg Cys
385                 390                 395                 400

Asp Arg Gly Gly Phe Trp Ala Asp Asp Tyr Ser Arg Cys Gln Tyr
            405                 410                 415

Ala Asn Asp Val Thr Arg Val Leu Tyr Met Phe Asn Gln Met Pro Leu
        420                 425                 430

Asn Leu Thr Asn Ala Val Ala Thr Ala Arg Gln Leu Leu Ala Tyr Thr
    435                 440                 445

Val Glu Ala Ala Asn Phe Ser Asp Lys Met Asp Val Ile Phe Val Ala
450                 455                 460

Glu Met Ile Glu Lys Phe Gly Arg Phe Thr Lys Glu Glu Lys Ser Lys
465                 470                 475                 480

Glu Leu Gly Asp Val Met Val Asp Ile Ala Ser Asn Ile Met Leu Ala
            485                 490                 495

Asp Glu Arg Val Leu Trp Leu Ala Gln Arg Glu Ala Lys Ala Cys Ser
        500                 505                 510

Arg Ile Val Gln Cys Leu Gln Arg Ile Ala Thr Tyr Arg Leu Ala Gly
    515                 520                 525

Gly Ala His Val Tyr Ser Thr Ile Asp Phe Ser Ile His Pro Ile
    530                 535                 540

Leu Leu Trp Lys Leu Met Ser Ser Ser Leu Leu Ala Ser Arg Gly
545                 550                 555

<210> SEQ ID NO 5
<211> LENGTH: 975
<212> TYPE: PRT
<213> ORGANISM: Homo sapiens

<400> SEQUENCE: 5

Gln Gly Asn Ala Ser Lys Lys Val Glu Ile Val Leu Glu Thr Ser
  1               5                  10                  15

Ala Ser Tyr Cys Pro Ala Glu Arg Val Ala Asn Asn Arg Gly Asp Phe
            20                  25                  30

Arg Trp Pro Arg Thr Leu Ala Gly Ile Thr Ala Tyr Gln Ser Cys Leu
        35                  40                  45

Gln Tyr Pro Phe Thr Ser Val Pro Leu Gly Gly Ala Pro Gly Thr
    50                  55                  60

Arg Ala Ser Arg Arg Cys Asp Arg Ala Gly Arg Trp Glu Pro Gly Asp
65                  70                  75                  80

Tyr Ser His Cys Leu Tyr Thr Asn Asp Ile Thr Arg Val Leu Tyr Thr
                85                  90                  95

Phe Val Leu Met Pro Ile Asn Ala Ser Asn Ala Leu Thr Leu Ala His
            100                 105                 110

Gln Leu Arg Val Tyr Thr Ala Glu Ala Ala Ser Phe Ser Asp Met Met
        115                 120                 125

Asp Val Val Tyr Val Ala Gln Met Ile Gln Lys Phe Leu Gly Tyr Val
    130                 135                 140
```

```
Asp Gln Ile Lys Glu Leu Val Glu Val Met Val Asp Met Ala Ser Asn
145                 150                 155                 160

Leu Met Leu Val Asp Glu His Leu Leu Trp Leu Ala Gln Arg Glu Asp
            165                 170                 175

Lys Ala Cys Ser Arg Ile Val Gly Ala Leu Glu Arg Ile Gly Gly Ala
        180                 185                 190

Ala Leu Ser Pro His Ala Gln His Ile Ser Val Asn Ala Arg Asn Val
    195                 200                 205

Ala Leu Glu Ala Tyr Leu Ile Lys Pro His Ser Tyr Val Gly Leu Thr
210                 215                 220

Cys Thr Ala Phe Gln Arg Arg Glu Gly Gly Val Pro Gly Thr Arg Pro
225                 230                 235                 240

Gly Ser Pro Gly Gln Asn Pro Pro Glu Pro Glu Pro Pro Ala Asp
                245                 250                 255

Gln Gln Leu Arg Phe Arg Cys Thr Thr Gly Arg Pro Asn Val Ser Leu
                260                 265                 270

Ser Ser Phe His Ile Lys Asn Ser Val Ala Leu Ala Ser Ile Gln Leu
            275                 280                 285

Pro Pro Ser Leu Phe Ser Ser Leu Pro Ala Ala Leu Ala Pro Val
290                 295                 300

Pro Pro Asp Cys Thr Leu Gln Leu Leu Val Phe Arg Asn Gly Arg Leu
305                 310                 315                 320

Phe His Ser His Ser Asn Thr Ser Arg Pro Gly Ala Ala Gly Pro Gly
                325                 330                 335

Lys Arg Arg Gly Val Ala Thr Pro Val Ile Phe Ala Gly Thr Ser Gly
            340                 345                 350

Cys Gly Val Gly Asn Leu Thr Glu Pro Val Ala Val Ser Leu Arg His
        355                 360                 365

Trp Ala Glu Gly Ala Glu Pro Val Ala Ala Trp Trp Ser Gln Glu Gly
    370                 375                 380

Pro Gly Glu Ala Gly Gly Trp Thr Ser Glu Gly Cys Gln Leu Arg Ser
385                 390                 395                 400

Ser Gln Pro Asn Val Ser Ala Leu His Cys Gln His Leu Gly Asn Val
                405                 410                 415

Ala Val Leu Met Glu Leu Ser Ala Phe Pro Arg Glu Val Gly Gly Ala
            420                 425                 430

Gly Ala Gly Leu His Pro Val Val Tyr Pro Cys Thr Ala Leu Leu Leu
        435                 440                 445

Leu Cys Leu Phe Ala Thr Ile Ile Thr Tyr Ile Leu Asn His Ser Ser
    450                 455                 460

Ile Arg Val Ser Arg Lys Gly Trp His Met Leu Leu Asn Leu Cys Phe
465                 470                 475                 480

His Ile Ala Met Thr Ser Ala Val Phe Ala Gly Gly Ile Thr Leu Thr
                485                 490                 495

Asn Tyr Gln Met Val Cys Gln Ala Val Gly Ile Thr Leu His Tyr Ser
                500                 505                 510

Ser Leu Ser Thr Leu Leu Trp Met Gly Val Lys Ala Arg Val Leu His
            515                 520                 525

Lys Glu Leu Thr Trp Arg Ala Pro Pro Gln Glu Gly Asp Pro Ala
530                 535                 540

Leu Pro Thr Pro Ser Pro Met Leu Arg Cys Trp Leu Val Trp Arg Pro
545                 550                 555                 560

Ser Leu Gly Ala Phe Tyr Ile Pro Val Ala Leu Ile Leu Leu Ile Thr
                565                 570                 575
```

-continued

Trp Ile Tyr Phe Leu Cys Ala Gly Leu Arg Leu Arg Gly Pro Leu Ala
            580                 585                 590

Gln Asn Pro Lys Ala Gly Asn Ser Arg Ala Ser Leu Glu Ala Gly Glu
        595                 600                 605

Glu Leu Arg Gly Ser Thr Arg Leu Arg Gly Ser Gly Pro Leu Leu Ser
610                 615                 620

Asp Ser Gly Ser Leu Leu Ala Thr Gly Ser Ala Arg Val Gly Thr Pro
625                 630                 635                 640

Gly Pro Pro Glu Asp Gly Asp Ser Leu Tyr Ser Pro Gly Val Gln Leu
                645                 650                 655

Gly Ala Leu Val Thr Thr His Phe Leu Tyr Leu Ala Met Trp Ala Cys
            660                 665                 670

Gly Ala Leu Ala Val Ser Gln Arg Trp Leu Pro Arg Val Val Cys Ser
        675                 680                 685

Cys Leu Tyr Gly Val Ala Ala Ser Ala Leu Gly Leu Phe Val Phe Thr
    690                 695                 700

His His Cys Ala Arg Arg Arg Asp Val Arg Ala Ser Trp Arg Ala Cys
705                 710                 715                 720

Cys Pro Pro Ala Ser Pro Ala Ala Pro His Ala Pro Pro Arg Ala Leu
                725                 730                 735

Pro Ala Ala Ala Glu Asp Gly Ser Pro Val Phe Gly Glu Gly Pro Pro
            740                 745                 750

Ser Leu Lys Ser Ser Pro Ser Gly Ser Ser His Pro Leu Ala Leu
        755                 760                 765

Gly Pro Cys Lys Leu Thr Asn Leu Gln Leu Ala Gln Ser Gln Val Cys
770                 775                 780

Glu Ala Gly Ala Ala Gly Gly Glu Gly Glu Pro Glu Pro Ala Gly
785                 790                 795                 800

Thr Arg Gly Asn Leu Ala His Arg His Pro Asn Asn Val His His Gly
                805                 810                 815

Arg Arg Ala His Lys Ser Arg Ala Lys Gly His Arg Ala Gly Glu Ala
            820                 825                 830

Cys Gly Lys Asn Arg Leu Lys Ala Leu Arg Gly Ala Ala Gly Ala
        835                 840                 845

Leu Glu Leu Leu Ser Ser Glu Ser Gly Ser Leu His Asn Ser Pro Thr
850                 855                 860

Asp Ser Tyr Leu Gly Ser Ser Arg Asn Ser Pro Gly Ala Gly Leu Gln
865                 870                 875                 880

Leu Glu Gly Glu Pro Met Leu Thr Pro Ser Gly Ser Asp Thr Ser
                885                 890                 895

Ala Ala Pro Leu Ser Glu Ala Gly Arg Ala Gly Gln Arg Arg Ser Ala
            900                 905                 910

Ser Arg Asp Ser Leu Lys Gly Gly Ala Leu Glu Lys Glu Ser His
        915                 920                 925

Arg Arg Ser Tyr Pro Leu Asn Ala Ala Ser Leu Asn Gly Ala Pro Lys
930                 935                 940

Gly Gly Lys Tyr Asp Asp Val Thr Leu Met Gly Ala Glu Val Ala Ser
945                 950                 955                 960

Gly Gly Cys Met Lys Thr Gly Leu Trp Lys Ser Glu Thr Thr Val
                965                 970                 975

<210> SEQ ID NO 6
<211> LENGTH: 11
<212> TYPE: PRT
<213> ORGANISM: Human immunodeficiency virus type 1

```
<400> SEQUENCE: 6

Tyr Gly Arg Lys Lys Arg Arg Gln Arg Arg
 1               5                  10

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence:
      internalizing domain derived from HIV tat protein

<400> SEQUENCE: 7

Gly Gly Gly Gly Tyr Gly Arg Lys Lys Arg Arg Gln Arg Arg
 1               5                  10                  15

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 8
gtggtggttc atcaggatcc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 9
cttcactatt ccacccttgc                                               20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 10
gggcggtagg cgtgtacggt gg                                            22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 11
gcatgtcaac agctcctgc                                                19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 12
ccagactgag tatcttttg                                                19
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 13
gcaatgcgct gaagacactg                                          20

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 14
aggtgacgtg atggttgac                                           19

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 15
gtggtggttc atcaggatcc                                          20

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: PCR primer

<400> SEQUENCE: 16
gggaggggtc acagggatg                                           19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 17
cttcactatt ccacccttgc                                          20
```